(12) United States Patent
Saint-Remy

(10) Patent No.: US 9,394,517 B2
(45) Date of Patent: Jul. 19, 2016

(54) CD4+ T-CELLS WITH CYTOLYTIC PROPERTIES

(71) Applicant: LIFE SCIENCES RESEARCH PARTNERS VZW, Leuven (BE)

(72) Inventor: Jean-Marie Saint-Remy, Grez-Doiceau (BE)

(73) Assignee: IMCYSE SA, Sart-Tilman (BE)

( * ) Notice: Subject to any disclaimer, the term of this patent is extended or adjusted under 35 U.S.C. 154(b) by 109 days.

(21) Appl. No.: 14/135,630

(22) Filed: Dec. 20, 2013

(65) Prior Publication Data

US 2014/0186297 A1 Jul. 3, 2014

Related U.S. Application Data

(63) Continuation of application No. 12/735,741, filed as application No. PCT/EP2009/051807 on Feb. 16, 2009, now abandoned.

(60) Provisional application No. 61/035,908.

(30) Foreign Application Priority Data

Feb. 14, 2008 (EP) .................... 08447006

(51) Int. Cl.
 *C12N 5/0783* (2010.01)
 *A61K 35/12* (2015.01)
 *A61K 39/00* (2006.01)

(52) U.S. Cl.
 CPC ......... *C12N 5/0636* (2013.01); *A61K 2035/124* (2013.01); *A61K 2039/57* (2013.01); *A61K 2039/627* (2013.01); *C12N 2501/23* (2013.01)

(58) Field of Classification Search
None
See application file for complete search history.

(56) References Cited

U.S. PATENT DOCUMENTS

| | | | |
|---|---|---|---|
| 4,886,782 A | 12/1989 | Good et al. | |
| 5,633,234 A | 5/1997 | August et al. | |
| 5,863,528 A | 1/1999 | Hawley et al. | |
| 6,602,509 B1 | 8/2003 | Saint-Remy et al. | |
| 6,759,046 B1 | 7/2004 | Gaudernack et al. | |
| 7,157,089 B1 | 1/2007 | Mizzen et al. | |
| 2003/0049723 A1 | 3/2003 | Zhang et al. | |
| 2003/0104570 A1 | 6/2003 | Cabezon Silva et al. | |
| 2003/0129205 A1 | 7/2003 | Saint-Remy et al. | |
| 2003/0152581 A1 | 8/2003 | Saint-Remy et al. | |
| 2004/0077045 A1 | 4/2004 | Zhang et al. | |
| 2005/0107256 A1 | 5/2005 | Barnwell et al. | |
| 2005/0196386 A1 | 9/2005 | Blazar et al. | |
| 2005/0202044 A1 | 9/2005 | Mizzen et al. | |
| 2006/0211091 A1 | 9/2006 | Zhang et al. | |
| 2006/0216301 A1 | 9/2006 | Tahara et al. | |
| 2006/0269561 A1 | 11/2006 | Paterson et al. | |
| 2007/0160620 A1 | 7/2007 | Mizzen et al. | |
| 2010/0068193 A1* | 3/2010 | Brunsvig ............. C12N 5/0636 424/93.71 |
| 2010/0203083 A1 | 8/2010 | Lux et al. | |
| 2010/0330088 A1 | 12/2010 | Saint-Remy | |
| 2011/0002903 A1 | 1/2011 | Saint-Remy | |
| 2011/0110964 A1 | 5/2011 | Saint-Remy | |
| 2011/0111395 A1 | 5/2011 | Saint-Remy | |
| 2011/0111502 A1 | 5/2011 | Saint-Remy | |
| 2012/0009678 A1 | 1/2012 | Saint-Remy | |

FOREIGN PATENT DOCUMENTS

| | | |
|---|---|---|
| JP | 2004-147649 | 5/2004 |
| WO | WO 93/08279 | 4/1993 |
| WO | WO 99/58552 | 11/1999 |
| WO | WO 01/70263 | 9/2001 |
| WO | WO 02/00892 | 1/2002 |
| WO | WO 02/095051 | 11/2002 |
| WO | WO 2004/018667 | 3/2004 |
| WO | WO 2004/024766 | 3/2004 |
| WO | WO 2005/012502 | 2/2005 |
| WO | WO 2005/039613 | 5/2005 |
| WO | WO 2005/086781 | 9/2005 |
| WO | WO 2006/059529 | 6/2006 |
| WO | WO 2007/104715 | 9/2007 |
| WO | WO 2008/017517 | 2/2008 |
| WO | WO2009/100505 | 8/2009 |
| WO | WO 2009/101204 | 8/2009 |
| WO | WO2009/101205 | 8/2009 |
| WO | WO2009/101206 | 8/2009 |
| WO | WO2009/101207 | 8/2009 |
| WO | WO2009/101208 | 8/2009 |

OTHER PUBLICATIONS

Lindqvist et al., 2011, Immunology, vol. 133: 296-306.*
Crellin et al., 2007, Blood, vol. 109: 2014-2022.*
Peterson, 2012, Toxic. Path. vol. 40: 186-204.*
Carlier et al., Jun. 2007, Munksgaard Allergy, vol. 62, p. 555.*
Aleksza et al "Altered cytokine expression of peripheral blood lymphocytes in polymyositis and dermatomyositis", (2005) Ann. Rheum. Dis. 64, 1485-1489.
Arunalacham et al, Enzymatic reduction of disulfide bonds in lysosomes: Characterization of a Gamma-interferon-inducible lysosomal thiol reductase (GILT), (2000) Proc. Natl. Acad. Sci USA, vol. 97, No. 2, 745-750.
Bolivar et al, "Molecular Cloning of a Zinc Finger Autoantigen Transiently Associated with Interphae Nucleolus and Mitotic Centromeres and Midbodies", J. (1999) J. Biol Chem., vol. 274, No. 51, 36456-36464.
Bower et al "Two Members of the Thioredoxin-h Family Interact with the Kinase Domain of a Brassica S Locus Receptor Kinase", (1996) The plant cell, vol. 8, 1641-1650.
Braun et al, "Acute Rejection in the Absence of Cognate Recognition of Allograft by T Cells" (2001) J.Immunol. 166(8), 4879-4883.
Brinks et al, "Immunogenicity of Therapeutic Proteins: The Use of Animal Models", (2011) Phar res 28,2379-2385.

(Continued)

*Primary Examiner* — Amy Juedes
(74) *Attorney, Agent, or Firm* — Nixon & Vanderhye P.C.

(57) ABSTRACT

The present invention relates to CD4+ T cells, more specifically cytolytic or cytotoxic CD4+ T-cells and methods of obtaining and identifying them.

6 Claims, 17 Drawing Sheets

(56) References Cited

OTHER PUBLICATIONS

Figure 1:
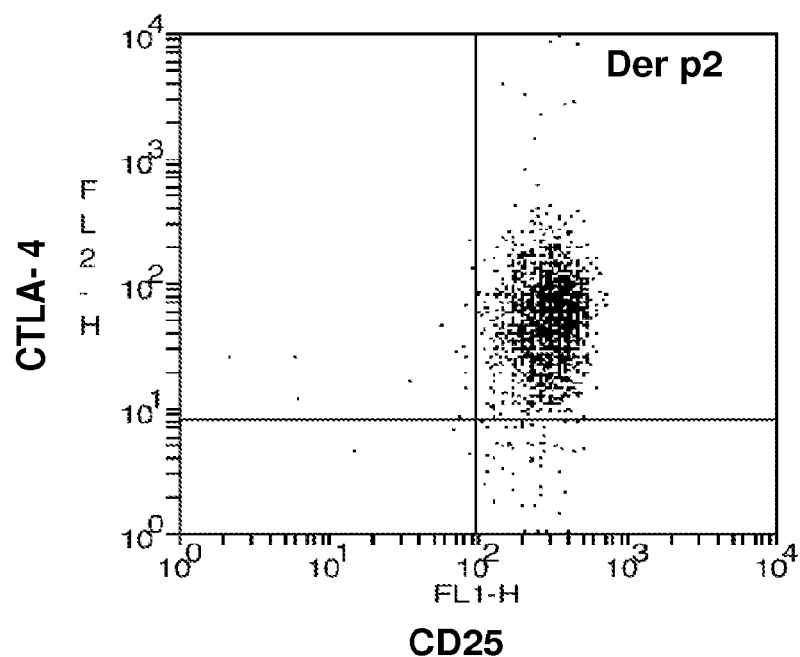
Figure 1:
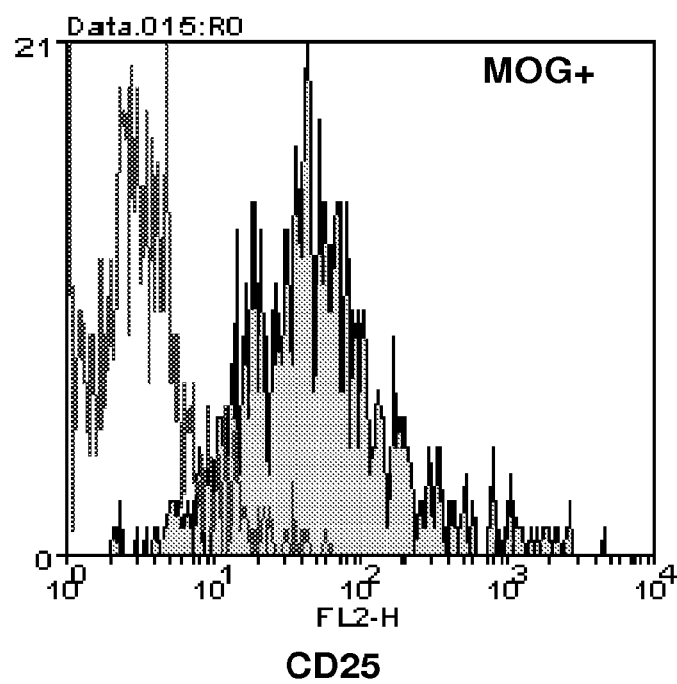
Figure 1:
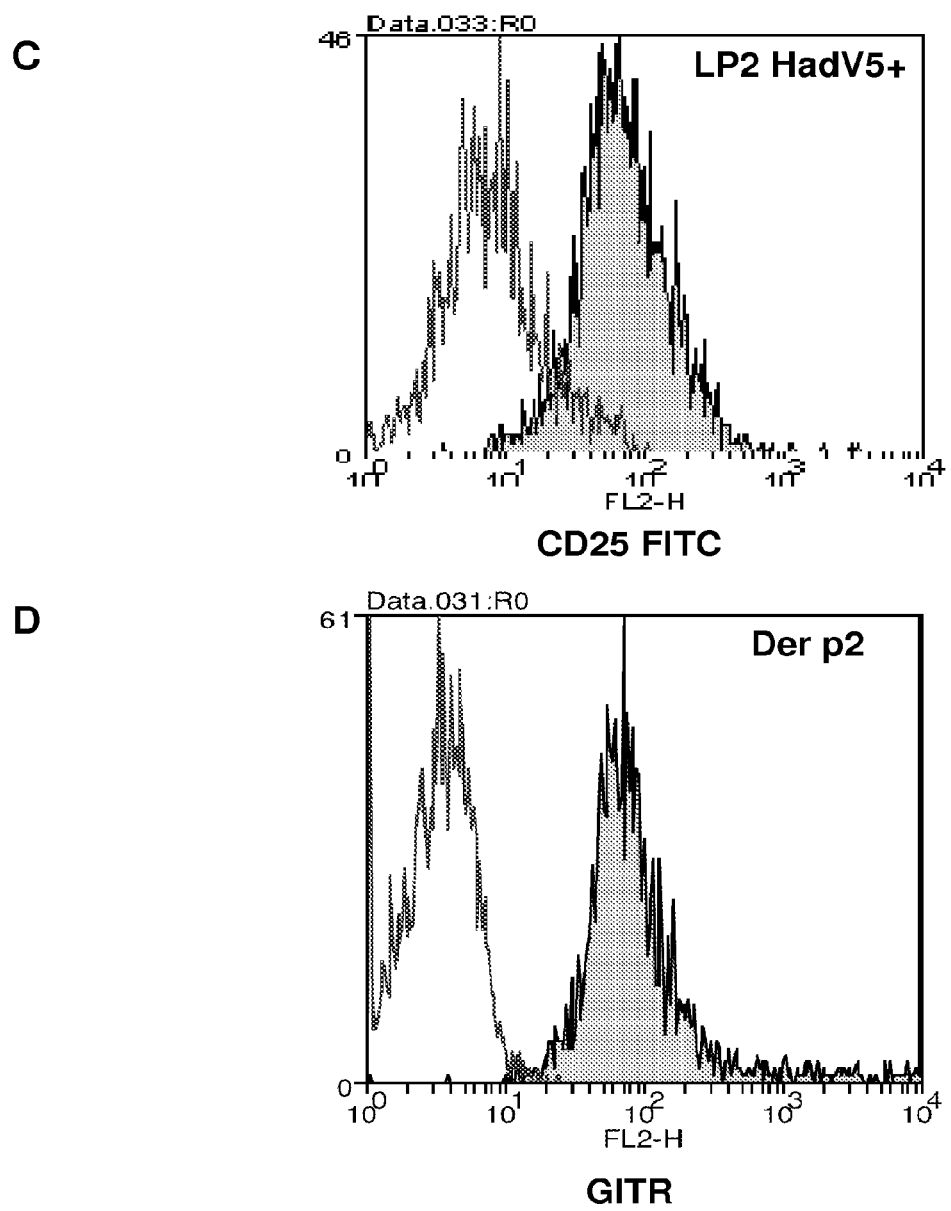
Figure 1:
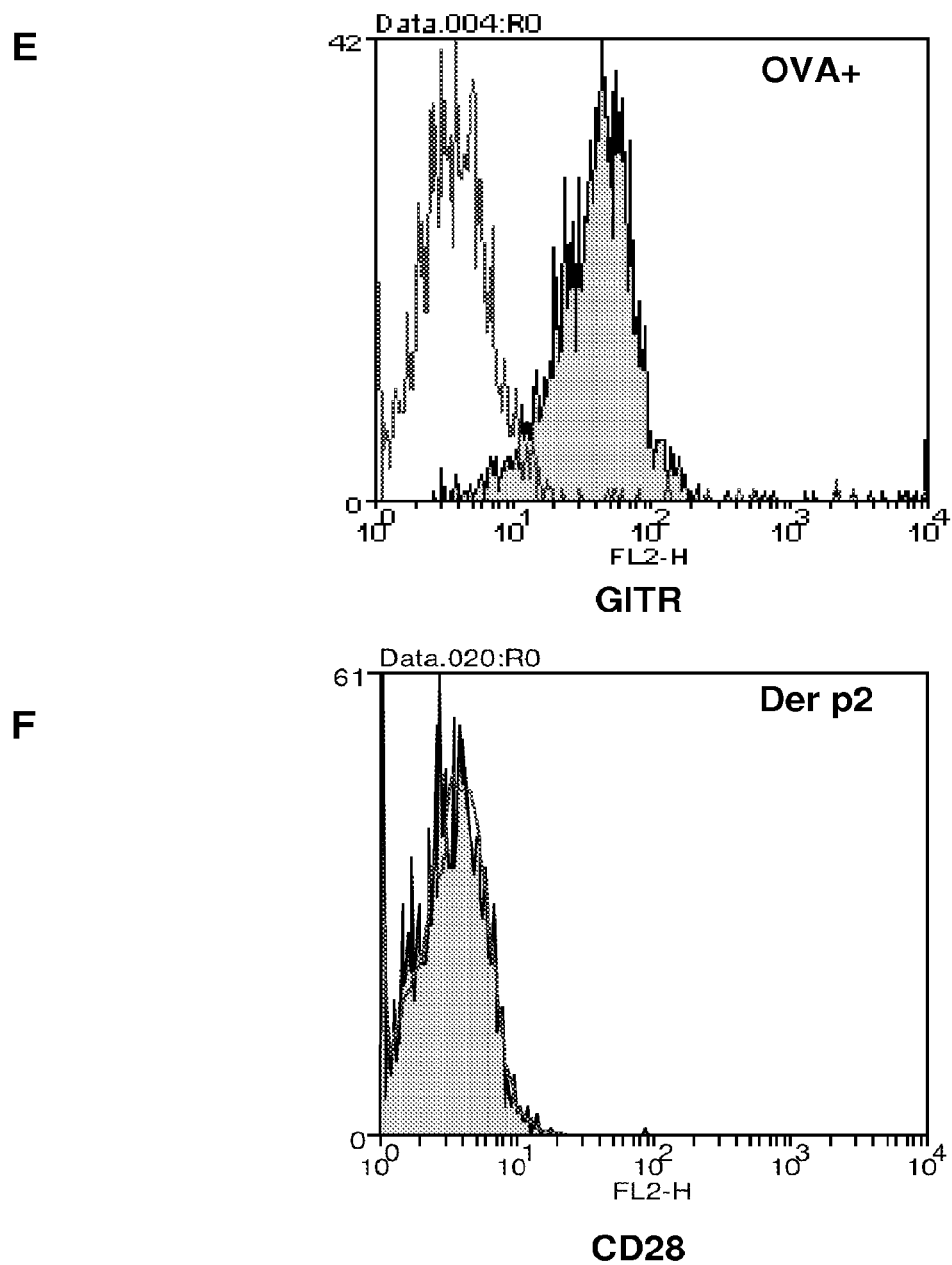
Figure 1:
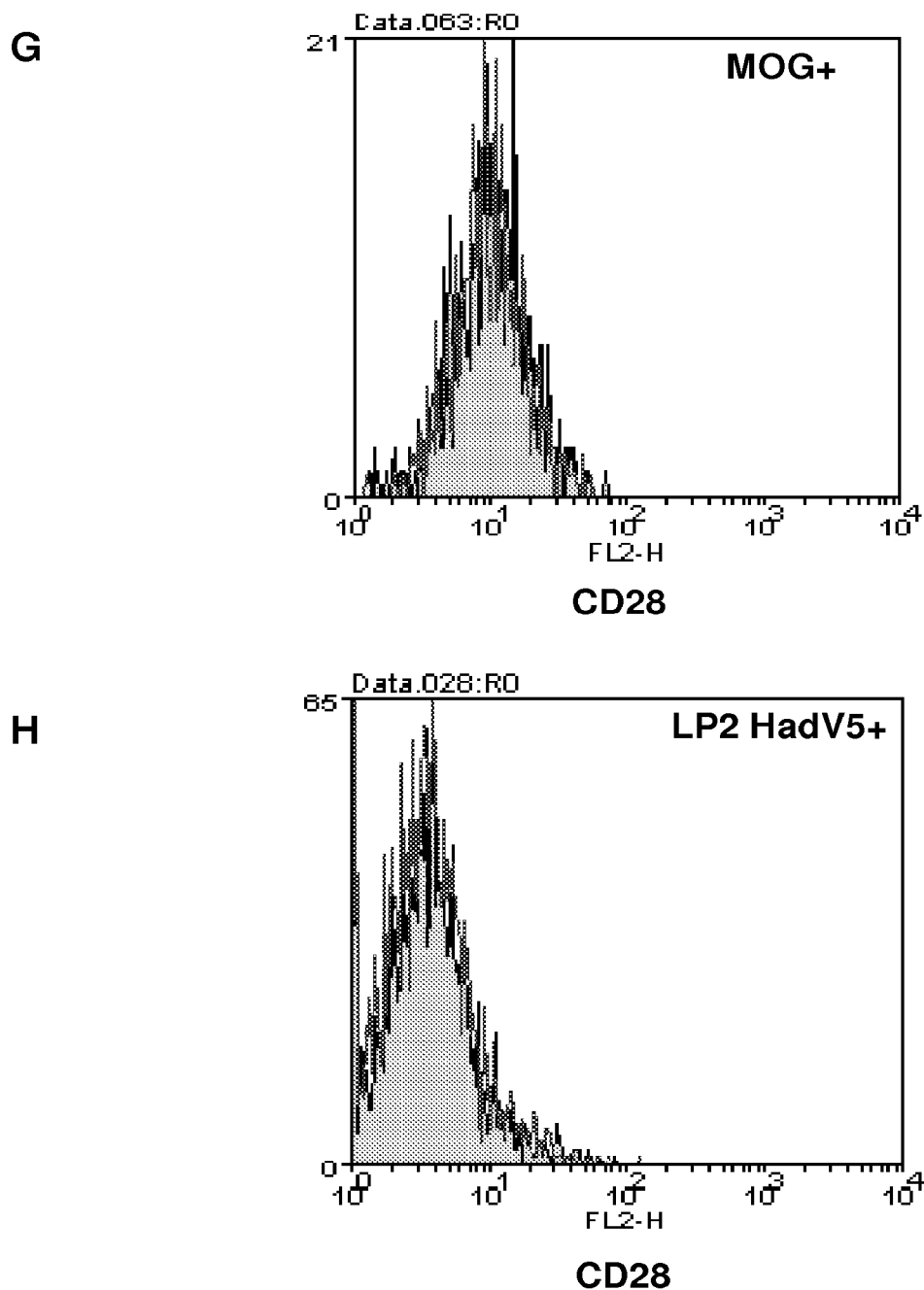

Brinster et al, "Brinster et al, Bone Marow-Derived Dendritic Cells Reverse the Anergic State of CD4+CD25+ T Cells without Reversing Their Suppressive Function", (2005), The Journal of Immunology 175:7332-7340.
Brinster et al, "Costimulatory effects of IL-1 on the expansion/differentiation of CD4+CD25+Foxp3+ and CD4+CD25+Foxp3 T cells", (2008) J. Leukoc. Biol. 84:480-487.
Cao et al "Prevention of Gene Transfer-Induced Inhibitor Formation by Nasal Administratn of Human F.IX T Cell Epitope in a Murine Model of Hemophilia B", (2004) Blood 104, 121a-122a.
Capon et al, "The CD4-gp120 Interaction and Aids Pathogenesis" (1991) Ann. Rev. Immunol 9, 649-678.
Carlier et al, "Increased Synapse Formation Obtained by T Cell Epitopes Containing a CxxC Motif in Flanking Residues Convert CD4+ T Cells into Cytolytic Effectors", 2012 PlosOne vol. 7, Issue 10, e45366.
Chen et al, "Glucocorticoid amplifies Il-2-dependent expansion of functional FoxP3+CD4+CD25+ T regulatory cells in vivo and enhances their capacity to suppress EAE", (2006) Eur. J. Immunol. 36, 2139-2149.
Chen et al, "Induction of dominant transplanation tolerance by an altered peptide ligand of the male antigen Dby", (2004) J Clin. Invest. 113(12), 1754-1762.
Corthay et a "CD4+ T Cells Cooperate with Macrophages for Specific Elimination of MHC Class II-Negative Cancer Cells", (2007) Adv Exp Med Biol. 590, 195-208.
Crompton et al, "Advances and challenges in malaria vaccine development", (2010) J. Clin. Invest., vol. 120, No. 12, 4168-4178.
Davids et al, "A New Family of Giardial Cysteine-Rich Non-VSP Protein Genes and a Novel Cyst Protein", (2006) Plos. One. 1, E44, 1-12.
De La Cruz, "The Immunologic Significance of Variation Within Malaria Circumsporozoite Protein Sequences", (1989) V. J. Immunol., vol. 142, No. 10, 3568-3575.
Dobrzanski, "Expanding roles for CD4T cells and their subpopulations in tumor immunity and therapy", (2013) Front. Oncology, vol. 3, Article 63, 1-19.
Dobrzynski, "Prevention of cytotoxic T lymphocyte responses to factor IX-expressing hepatocytes by gene transfer-induced regulatory T cells", (2006) Proc. Natl. Acad Sci. U.S.A., vol. 103, No. 12, 4592-4597.
Eberl et al, "Tissue-Specific Segregation of CD1d-Dependent and CD1d-Independent NK T Cells", (1999) J. Immunol. 162, 6410-6419.
Fan et al, "Co-immunization of BALB/c mice with recombinant immunogens containing G protein fragment and chimeric CTL epitope of respiratory syncytial virus induces enhanced cellular immunity and high level of antibody response", (2005) Vaccine 23, 4453-4461.
Fomenko et al "Identity and Functions of CxxC-Derived Motifs", (2003) Biochem. 42, 11214-11225.
Ge et al, "An hsp 70 fusion protein vaccine potentiates the immune response against Japanese encephalitis virus", (2007) Arch. Viral 152, 125-135.
Geluk et al, "HLA-DR Binding Analysis of Peptides From Islet Antigens in IDDM", (1998) Diabetes 47, 1594-1601.
Gentile et al, "Thyroglobulin as an autoantigen: what can we learn about immunopathogenicity from the correlation of antigenic properties with protein structure?", (2004) Immunol 112 13-25.
Gross et al, "Simple conditioning with monospecific CD4+CD25+ regulatory T cells for bone marrow engraftment and tolerance to multiple gene products", (2006) Blood 108(6), 1841-1848.
Grossman et al, "Differential expression of granzymes A and B in human cytotoxic lymphocyte subsets and T regulatory cells", (2004) Blood, vol. 104, No. 9, 2840-2848.
Hague, "Cysteinylation of MHC Class II Ligands: Peptide Endocytosis and Reduction Within APC Influences T Cell Recognition 1", (2001) J. Immunol. 166, 4543-4551.
Harris, Prediction of murine MHC class I epitopes in a major house dust mite allergen and induction of T1-type CD8+ T cell responses, (1997) Int. Immunol., vol. 9, No. 2, 273-280.
Haveman, "Induction and Capture of CD4+ Cytotoxic Adenoviral Specific T-Cells in Response to pan-DR Binding Adenoviral Epitopes; towards Immunotherapy", (2005) Blood 106, Abstract 3238.
Hohn, "CD4+ Tumor-Infiltrating Lymphocytes in Cervical Cancer Recognize HLA-DR-Restricted Peptides Provided by Human Papillomavirus-E7", (1999) The Journal of Immunology 163, 5715-5722.
Hori et al, "Control of Regulatory T Cell Development by the Transcription Factor Foxp3" (2003) Science 299, 1057-1061.
Hsu et al, "Assessing Computational Amino Acid β-Turn Propensities with a Phage-Displayed Combinatorial Library and Directed Evolution", (2006) Structure 14(10):1499-510.
Ise et al, "Naive CD4+ T Cells Exhibit Distinct Expression Patterns of Cytokines and Cell Surface Molecules on Their Primary Responses to Varying Doses of Antigen", (2002) J. Immunol. 168, 3242-3250.
James et al, "HY peptides modulate transplantation responses to skin allografts", (2002) Int. Immunol. 14(11), 1333-1342.
Janssens et al, "CD4+ CD25+ T Cells Lyse Antigen-Presenting B Cells by Fas-Fas Ligand Interaction in an Epitope-Specific Manner[1]", (2003) J. Immunol. 171, 4604-4612.
Jensen, "Acidification and Disulfide Reduction Can be Sufficient to Allow Intact Proteins to Bind Class II MHC[1]", (1993) J. Immunol. 150, No. 8, 3347-3356.
Joffre et al, "Induction of antigen-specific tolerance to bone marrow allografts with CD4+ CD25+ T lymphocytes", (2004) Blood 103(11), 4216-4221.
Wobus et al, "Embryonic Stem Cells: Prospects for Developmental Biology and Cell Therapy", (2005) Physiol Rev 85: 635-678.
Khare et al, "HLA class II transgenic mice authenticate restriction of myelin oligodendrocyte glycoprotein-specific immune response implicated in multiple sclerosis pathogenesis", (2003) Int. Immunol. 15, No. 4, 535-546.
Li Pira et al, "High Throughput T Epitope Mapping and Vaccine Development", (2010) J. Biomed. and Biotechnol., vol. 2010, 325720.
Louis et al, "Contrasting CD25[hi]CD4[+] T Cells/FOXP3 Patterns in Chronic Rejection and Operational Drug-Free Tolerance", Transplantation 2006; vol. 81, No. 3, 398-407.
Mach et al, "Regulation of MHC Class II Genes: Lessons from a Disease", (1996) Ann. Rev. Immunol. 14, 301-331.
Maeda et al, "CD1d-Independent NKT Cells in $β_2$-Microglobulin-Deficient Mice Have Hybrid Phenotype and Function of NK and T Cells", (2004) J. Immunol. 172, 6115-6122.
Maekawa et al, "Evidence for a Domain-Swapped CD4 Dimer as the Coreceptor for Binding to Class II MHC[1]", (2006) J. Immunol. 176(11), 6873-6878.
Matthias et al, "Disulfide exchange in domain 2 of CD4 is required for entry of HIV-1", (2002) Nature immunol 3, No. 8, 727-732.
Maynard et al, "Regulatory T cells expressing interleukin 10 develop from Foxp3[+] and Foxp3[-] precursor cells in the absence of interleukin 10", (2007) Nat. Immunol. 8, No. 9, 931-941.
Okubo et al, "Analysis of HLA-DRB1*0901-binding HPV-16 E7 helper T cell epitopel", (2004) J Obstet Gynaecol Res. 30(2), 120-129.
Oliviera et al, "Insights into the Specificity of Thioredoxin Reductase—Thioredoxin Interactions. A Structural and Functional Investigation of the Yeast Thioredoxin System", (2010) biochemistry 49, 3317-3326.
Park et al, "Redox Regulation Facilitates Optimal Peptide Selection by MHC Class I during Antigen Processing", (2006) cell 127, 369-372.
Qin et al, "Fusion protein of CDR mimetic peptide with Fc inhibit TNF-α induced cytotoxicity", (2006) Mol. Immunol. 43, 660-666.
Roep et al, "The problems and promises of research into human immunology and autoimmune disease", (2012) Nature Med 18(1) 48-53.
Roopenian et al, "The immunogenomics of minor histocompatibility antigens", (2002) Immunol. Rev. 190, 86-94.
Roper et al, "SARS vaccines: where are we?" (2009) Expert Rev. Vaccines 8(7), 887-898.

(56) References Cited

OTHER PUBLICATIONS

Saez-Borderias et al, "Expression and function of NKG2D in CD4+ T cells specific for human cytomegalovirus", (2006) Eur. J. Immunol. 36, 3198-3206.

Santin et al, "Human Papillomavirus Type 16 and 18 E7-Pulsed Dendritic Cell Vaccination of Stage IB or IIA Cervical Cancer Patients: a Phase I Escalating-Dose Trial", (2008) J. Virol. 82, No. 4, 1968-1979.

Savoldo et al, "Generation of EBV-Specific CD4+ Cytotoxic T Cells from Virus Naive Individuals[1]", (2002) J Immunol. 168(2), 909-918.

Sette et al, "HLA supertypes and supermotifs: a functional perspective on HLA polymorphism", (1998) Curr Opinion Immunol. 10, 478-482.

Shi et al, "A novel plasma membrane-bound thioredoxin from soybean", (1996) Plant Mol. Biol. 32, 653-662.

Stenstrom, "Natural killer T-cell populations in C57BL/6 and NK1.1 congenic BALB.NK mice—a novel thymic subset defined in BALB.NK mice", (2005) Immunol. 114, 336-345.

Sundar et al, "Generation of Epstein-Barr Virus Antigen-Specific Suppressor T Cells in Vitro", (1985) Int. J. Cancer 35, 351-357.

Taylor et al, "T regulatory cells and allergy", (2005) Microbes and Infection 7, 1049-1055.

Iqbalsyah et al, "The CXXC motif at the N terminus of an α-helical peptide", (2006) Protein Sci. 15, 1945-1950.

Texier et al, "On the diversity and heterogeneity of $H-2^d$-restricted determinants and T cell epitopes from the major bee venom allergen", (1999) Int Immunol. 11, 1313-1325.

Thomson et al, "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design", (1998) J. Virol 72(3) 2246-2252.

Tindle et al, "A "public" T-helper epitope of the E7 transforming protein of human papillomavirus 16 provides cognate help for several E7 B-cell epitopes from cervical cancer-associated human papillomavirus genotypes", (1991) Proc Natl. Acad. Sci 88, 5887-5891.

Tsuji et al, "Antigen-specific, CD4+CD25+ regulatory T cell clones induced in Peyer's patches", (2003) Int. Immunol. 15, No. 4, 525-534.

Voo, "Functional Characterization by EBV-Encoded Nuclear Antigen 1-Specific CD4+ Helper and Regulatory T Cells Elicited by in vitro Peptide Stimulation", (2005) Cancer Res. 65, 1577-1586.

Wang et al, "Immune suppression by tumor-specific CD4+ regulatory T-cells in cancer", (2006) Semin. Cancer Biol. 16, 73-79.

Weissert et al, "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis[1]", (2001) J. Immunol. 166, 7588-7599.

Wekerle et al, "Autoimmunity's next top models", (2012) Nature Med. 18(1), 66-70.

Wiker, "Cloning, expression and significance of MPT53 for identification of secreted proteins of *Mycobacterium tuberculosis*", (1999) Microb. Pathog. 26, 207-219.

Wood et al, "Regulatory T Cells in Transplantation Tolerance", (2003) Nat. Rev. Immunol. 3, 199-210.

Wu et al, "Engineering an intracellular pathway for major histocompatibility complex class II presentation of antigens", (1995) Proc. Natl. Acad. Sci. 92, 11671-11675.

Zhao et al, "Activated CD4+CD25+ T cells selectively kill B lymphocytes", (2006) Blood 107(10), 3925-3932.

Toyokawa et al, "Relative Contribution of Direct and Indirect Allorecognition in Developing Tolerance After Liver Transplantation", 2008 Liver Transpl. 14(3) 346-357.

Boisgerault et al, "Differential roles of direct and indirect allorecognition pathways in the rejection of skin and corneal transplants", (2009) Transplantation 87(1): 16-23.

Li et al, "Twisting immune responses for allogeneic stem cell therapy", (2009) World J Stem Cells 1(1), 30-35.

Batten et al, "Immune response to stem cells and strategies to induce tolerance", (2007) Phil. Trans. R. Soc. B 362, 1343-1356.

International Search Report for PCT/EP2009/051807, mailed Jul. 13, 2009.

* cited by examiner

A

B

B

C

D

E

F

G

NKG2D

C

CD4+ T-CELLS WITH CYTOLYTIC PROPERTIES

This application is a continuation of application Ser. No. 12/735,741 (abandoned), filed Aug. 13, 2010 (published as US 2011-0111395-A1), which is a U.S. national phase of International Application No. PCT/EP2009/051807, filed 16 Feb. 2009, which designated the U.S. and claims priority to European Application No. 08447006.1, filed 14 Feb. 2008 and U.S. Application No. 61/035,908, filed 12 Mar. 2008, the entire contents of each of which are hereby incorporated by reference.

FIELD OF THE INVENTION

The present invention relates to CD4+ T cells, more specifically cytolytic or cytotoxic CD4+ T-cells and methods of obtaining and identifying them.

BACKGROUND OF THE INVENTION

Natural regulatory T cells (Tregs) are actively selected in the thymus and exert potent suppressive activity in the periphery for the induction and maintenance of tolerance. These cells are characterised by a distinct phenotype including high expression of cell surface proteins CD25 and GITR, high intracellular expression of CTLA-4, but absence of IL-7R. They are anergic and hyporesponsive in the absence of exogenous growth factors, and do not produce IL-2. Expression of the transcription repressor Foxp3 is the hallmark of such natural Tregs. The suppressive activity of natural Tregs was shown to be linked to a defect in phosphorylation of AKT, a serine-threonine kinase dependent of phosphatidylinositide-3 kinase (PI3K; Crellin et al. (2007) *Blood* 109: 2014-2022).

The use of such natural Tregs in controlling immune disorders by adoptive cell transfer is severely limited by the very low frequency of cells of defined specificity, the difficulty to expand them in vitro and by the absence of efficient methods by which they can be expanded in vivo. Besides, the functional activity of natural regulatory T cells is non-specific, as they produce suppressive cytokines such as IL-10 and TGF-beta. Hence, there is a need for suppressor T cells with increased specificity that are in addition more amenable to expansion.

SUMMARY OF THE INVENTION

In one aspect, the current invention encompasses isolated populations of cytotoxic CD4+ T-cells (in either resting or activated state) characterised, when compared to natural CD4+ regulatory T-cells, by absence of expression or undetectable expression of the transcription repressor Foxp3. In a further embodiment, not excluding the previous embodiment, said population of cytotoxic CD4+ T-cells, in activated state/ upon antigenic stimulation, is, compared to natural CD4+ regulatory T-cells, further characterised by strong phosphorylation of PI3K and of AKT. In a further embodiment, not excluding the previous embodiments, said population of cytotoxic CD4+ T-cells is yet further characterised by production, upon antigenic stimulation, of high concentrations of IFN-gamma with variable concentrations of IL-4, IL-5, IL-10 and TNF-alpha (depending of the cytokine commitment of the corresponding effector clone), but no or undetectable production of IL-17 or TGF-beta, all when compared to natural CD4+ regulatory T-cells. More specifically, IL-10 concentrations of activated CD4+ T-cells according to the invention are significantly and drastically reduced compared to IL-10 concentrations in activated natural CD4+ regulatory T-cells. In a further embodiment, not excluding the previous embodiments, said population of cytotoxic CD4+ T-cells is yet further characterised by production, upon antigenic stimulation, of high concentrations of soluble FasL (Fas ligand) compared to natural CD4+ regulatory T-cells.

In a further aspect, the current invention encompasses isolated populations of cytotoxic CD4+ T-cells characterised, when compared to CD4+ effector T-cells, by constitutive expression (i.e. independent of whether the cytotoxic CD4+ T-cells are at rest or activated) of cell surface proteins CD25, GITR and intracellular CTLA-4, but no or undetectable expression of CD28 or CD127. In the present invention constitutive expression relates to the expression of a protein in cytotoxic CD4+ T-cells after a period of rest (i.e. no antigenic stimulation) of about 12 to 15 days. In a further embodiment, not excluding the previous embodiment, said population of cytotoxic CD4+ T-cells is, when compared to CD4+ effector T-cells, further characterised by expression of NKG2D. In a further embodiment, not excluding the previous embodiments, said population of cytotoxic CD4+ T-cells is, upon antigenic stimulation, yet further characterised by production of high concentrations of soluble FasL when compared to CD4+ effector T-cells. In a further embodiment, not excluding the previous embodiments, said population of cytotoxic CD4+ T-cells is, after antigenic stimulation, yet further characterised by combined expression of transcription factors T-bet and GATA3 when compared to CD4+ effector T-cells. In a further embodiment, not excluding the previous embodiments, said population of cytotoxic CD4+ T-cells is yet further characterised by absence of (detectable) IL-2 transcription when compared to CD4+ effector T-cells. In a further embodiment, not excluding the previous embodiments, said population of cytotoxic CD4+ T-cells is, when compared to CD4+ effector T-cells, yet further characterised by the capacity to induce apoptosis of APC, after antigenic stimulation by cognate interaction with peptide presented by MHC class II determinants. In a further embodiment, not excluding the previous embodiments, said population of cytotoxic CD4+ T-cells is, in comparison with CD4+ effector T-cells, yet further characterised by the capacity to induce apoptosis of bystander T cells.

In a further aspect, the current invention encompasses isolated populations of cytotoxic CD4+ T-cells characterised, when compared to NK-cells, by expression of the CD4 co-receptor. In a further embodiment, not excluding the previous embodiments, said population of cytotoxic CD4+ T-cells is, when compared to NK-cells, yet further characterised by absence of CD49b (as detected by binding of antibody DX5). These characteristics relative to NK-cells are independent of the activation status of the cytotoxic CD4+ T-cells and thus are detectable both in resting and activated cells.

In yet a further embodiment of the invention are comprised isolated populations of cytotoxic CD4+ T-cells characterised, when compared to NKT-cells by expression of an alpha-beta T cell receptor with invariant alpha chain and re-arranged beta chain. In a further embodiment, not excluding the previous embodiments, said population of cytotoxic CD4+ T-cells is, when compared to NKT-cells, further characterised by absence of (detectable) expression of the Valpha14 (mouse) or Valpha24 (human) TCR expression. In a further embodiment, not excluding the previous embodiments, said population of cytotoxic CD4+ T-cells is, in comparison with NKT-cells, yet further characterised by lack of CD1d restriction. These characteristics relative to NKT-cells are independent of the activation status of the cytotoxic CD4+ T-cells and thus are detectable both in resting and activated cells.

The invention comprises in another aspect isolated populations of cytotoxic CD4+ T-cells displaying any possible combination of any of the characteristics as described above and relative to natural CD4+ regulatory T-cells, CD4+ effector T-cells, NK-cells and/or NKT-cells or characterised by a combination of all of these characteristics.

The invention relates in another aspect to a method for obtaining or inducing populations of cytotoxic CD4+ T-cells as described above according to the invention, said methods comprising the steps of:
  (i) providing isolated natural naïve or memory CD4+ T-cells;
  (ii) contacting said cells with an immunogenic peptide comprising a T-cell epitope and, adjacent to said T-cell epitope or separated therefrom by a linker of at most 7 amino acids, a C-(X)2-[CST] or [CST]-(X)2-C motif; and
  (iii) expanding said cells in the presence of IL-2.

In a further aspect, the invention encompasses a method of identifying a population of cytotoxic CD4+ T-cells, said method comprising the steps of:
  (i) providing isolated natural CD4+ T-cells such as natural CD4+ regulatory T-cells, CD4+ effector cells, NK-cells or NKT-cells;
  (ii) providing CD4+ T-cells suspected of being cytotoxic; and
  (iii) determining that the T-cells provided in (ii) display, compared to the T-cells provided in (i), the respective characteristics as described above.

Thus, in one embodiment thereto, said method is identifying cytotoxic CD4+ T-cells by determining in step (iii) the absence of or undetectable expression of the transcription receptor Foxp3 when compared with expression of Foxp3 in natural CD4+ regulatory T-cells. Said method may further comprise determining in step (iii) that the T-cells provided in (ii) display, compared to natural CD4+ regulatory T-cells provided in (i), an increased kinase activity of the serine-threonine kinase AKT. In a further embodiment, not excluding the previous embodiment, said method is further comprising determining in step (iii) that the T-cells provided in (ii) display, compared to natural CD4+ regulatory T-cells provided in (i), undetectable production of TGF-beta and undetectable or very low production of IL-10. In a further embodiment, not excluding the previous embodiments, said method is further comprising determining in step (iii) that the T-cells provided in (ii) display, compared to natural CD4+ regulatory T-cells provided in (i), high concentrations of IFN-gamma production. In a further embodiment, not excluding the previous embodiments, said method is further comprising determining in step (iii) that the T-cells provided in (ii) display, compared to natural CD4+ regulatory T-cells provided in (i), production of high concentrations of soluble FasL.

In a further embodiment said method identifies populations of cytotoxic CD4+ T-cells according to the invention by comparing them with CD4+ effector cells. Thus, such methods may comprise determining in step (iii) that the T-cells provided in (ii) display, compared to CD4+ effector cells provided in (i), constitutive expression of cell surface proteins CD25, GITR and intracellular CTLA-4, but not of CD28 or CD127. In a further embodiment, not excluding the previous embodiments, said method is further comprising determining in step (iii) that the T-cells provided in (ii) display, compared to CD4+ effector cells provided in (i), expression of NKG2D on the cell surface. In a further embodiment, not excluding the previous embodiments, said method is further comprising determining in step (iii) that the T-cells provided in (ii) display, compared to CD4+ effector cells provided in (i), co-expression of transcription factors T-bet and GATA3. In a further embodiment, not excluding the previous embodiments, said method is further comprising determining in step (iii) that the T-cells provided in (ii) display, compared to CD4+ effector cells provided in (i), a absence of IL-2 transcription. In a further embodiment, not excluding the previous embodiments, said method is further comprising determining in step (iii) that the T-cells provided in (ii) display, compared to CD4+ effector cells provided in (i), the capacity to induce apoptosis of APC, after antigenic stimulation by cognate interaction with peptide presented by MHC class II determinants. In a further embodiment, not excluding the previous embodiments, said method is further comprising determining in step (iii) that the T-cells provided in (ii) display, compared to CD4+ effector cells provided in (i), the capacity to induce apoptosis of bystander T cells.

In a further embodiment said method identifies populations of cytotoxic CD4+ T-cells according to the invention by comparing them with NK-cells. Thus, such methods may comprise determining in step (iii) that the T-cells provided in (ii) display, compared to NK cells provided in (i), expression of the CD4 co-receptor. In a further embodiment, not excluding the previous embodiments, said method is further comprising determining in step (iii) that the T-cells provided in (ii) display, compared to NK cells provided in (i), the absence of expression of CD49b.

In a further embodiment of the invention are included methods for identifying populations of cytotoxic CD4+ T-cells according to the invention by comparing them to NKT-cells. Such methods may comprise determining in step (iii) that the T-cells provided in (ii) display, compared to NKT-cells provided in (i), expression of an alpha-beta T cell receptor with rearranged beta chain. In a further embodiment, not excluding the previous embodiments, said method is further comprising determining in step (iii) that the T-cells provided in (ii) display, compared to NKT-cells provided in (i), absence of expression of the Valpha14 (mouse) or Valpha24 (human) TCR expression. In a further embodiment, not excluding the previous embodiments, said method is further comprising determining in step (iii) that the T-cells provided in (ii) display, compared to the NKT-cells provided in (i), absence of CD1d restriction.

In the above methods according to the invention it is further possible to identify CD4+ T-cells suspected to be cytotoxic CD4+ T-cells according to the invention as provided in step (ii) by determining in step (iii) any possible combination of any or all of the characteristics as described above and relative to natural CD4+ regulatory T-cells, CD4+ effector T-cells, NK-cells and/or NKT-cells provided in step (i), said combinations also being described above.

FIGURE LEGENDS

FIG. 1. Cytolytic CD4+ T cell clones express markers associated with regulatory T cells. See Example 2 for detailed explanation.

Figure 2:
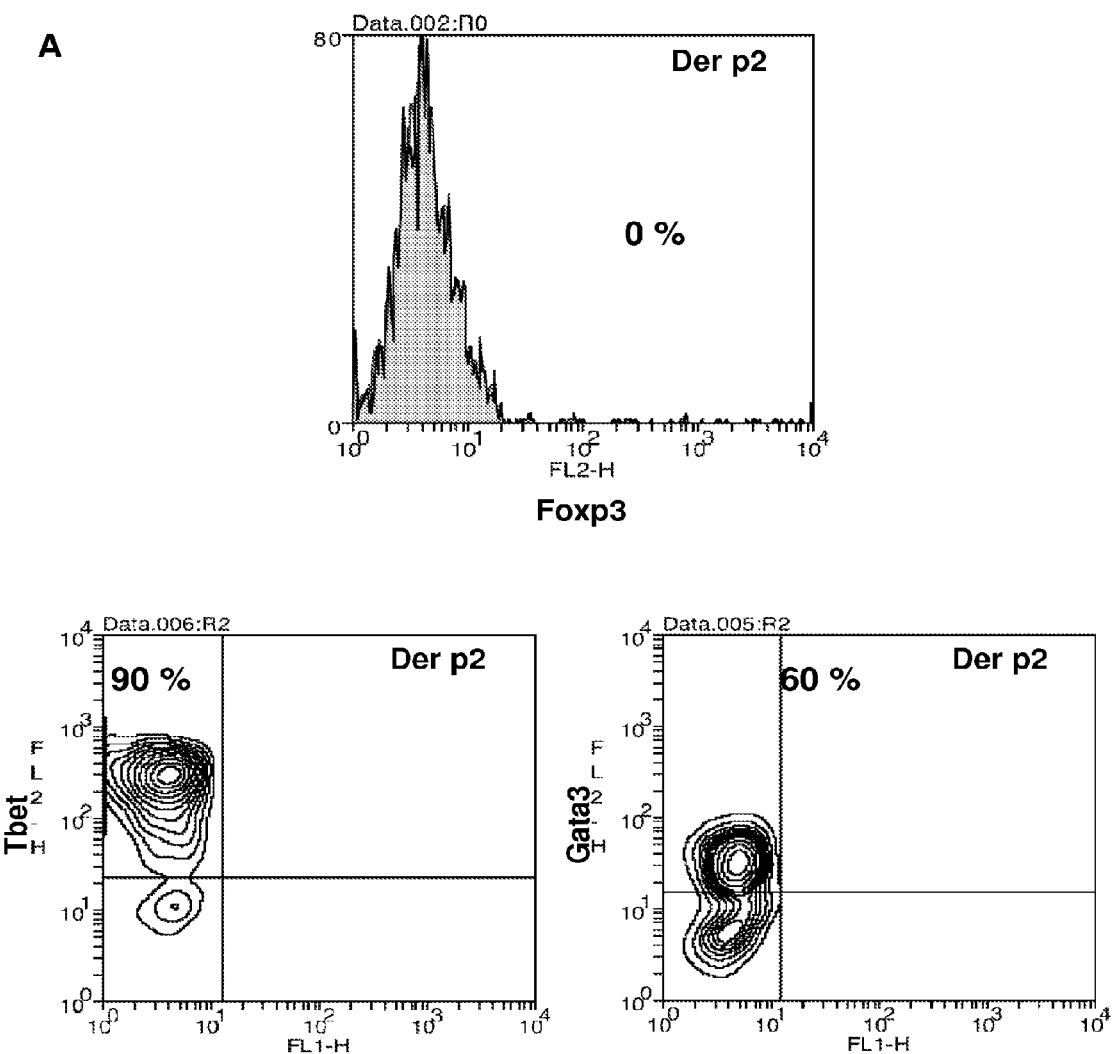
Figure 2:
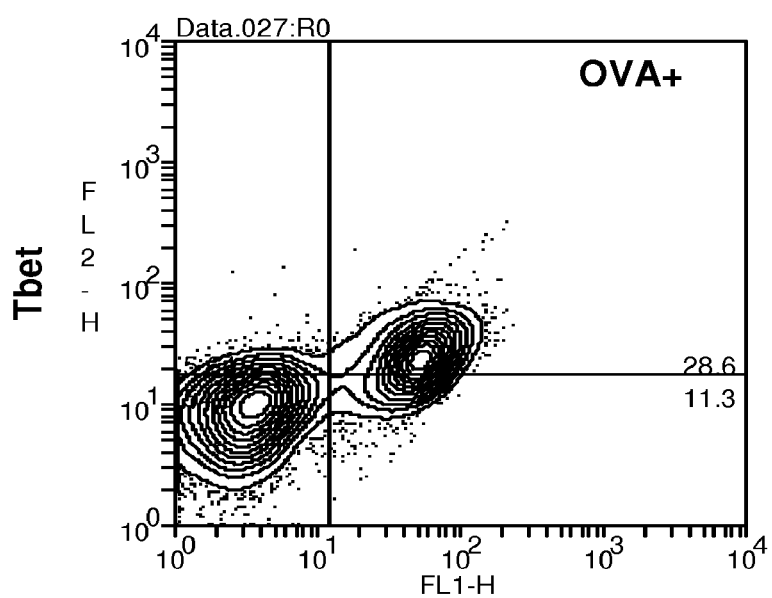
Figure 2:
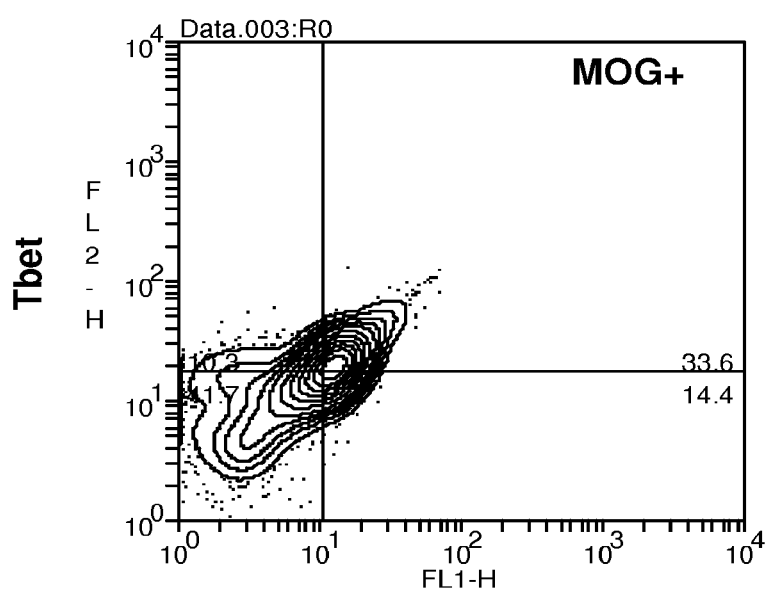

FIG. 2. Cytolytic CD4+ T cell clones co-express transcription factors T-bet and GATA3 but not Foxp3. See Example 3 for detailed explanation.

Figure 3:
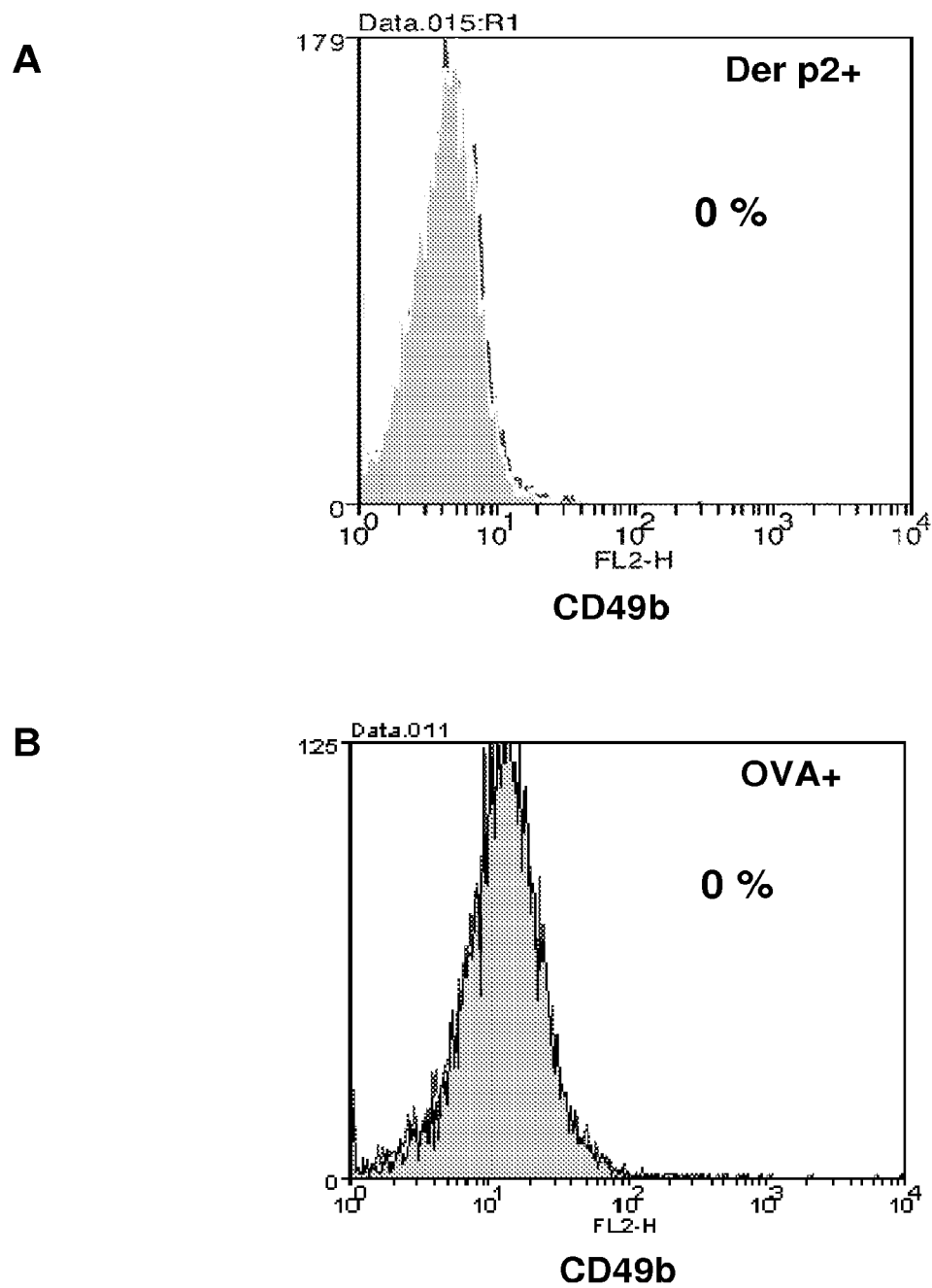
Figure 3:
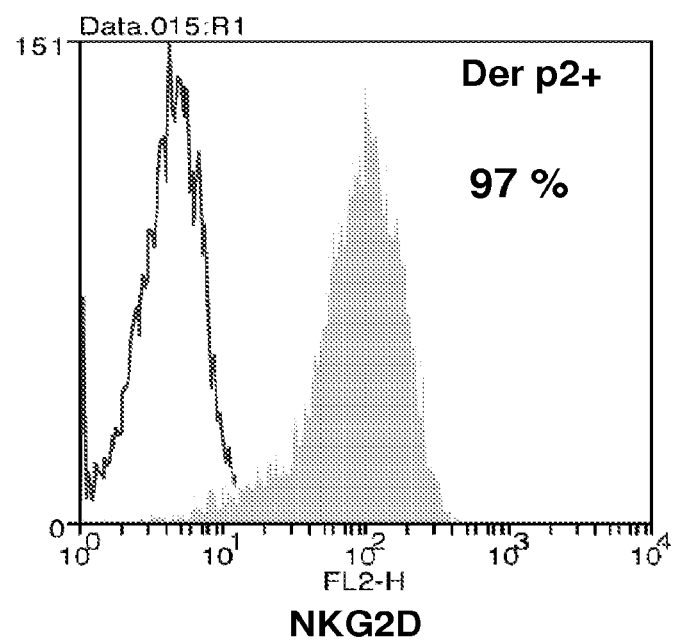
Figure 3:
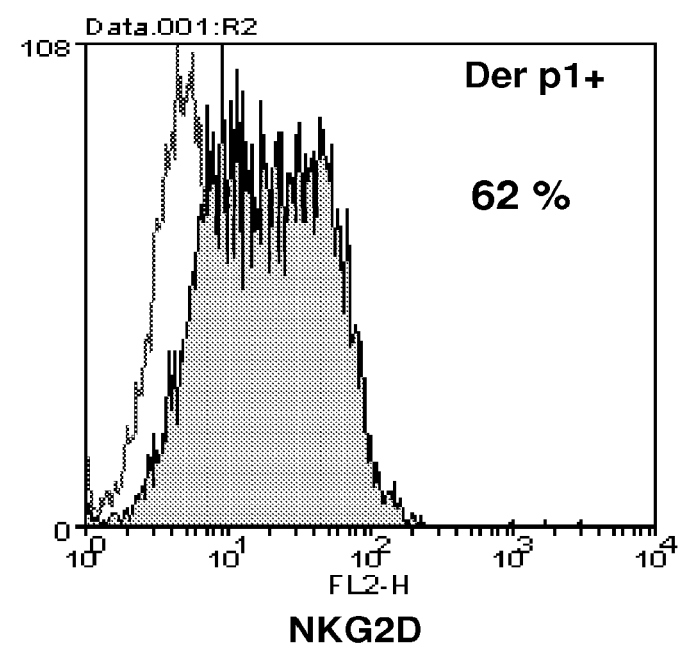
Figure 3:
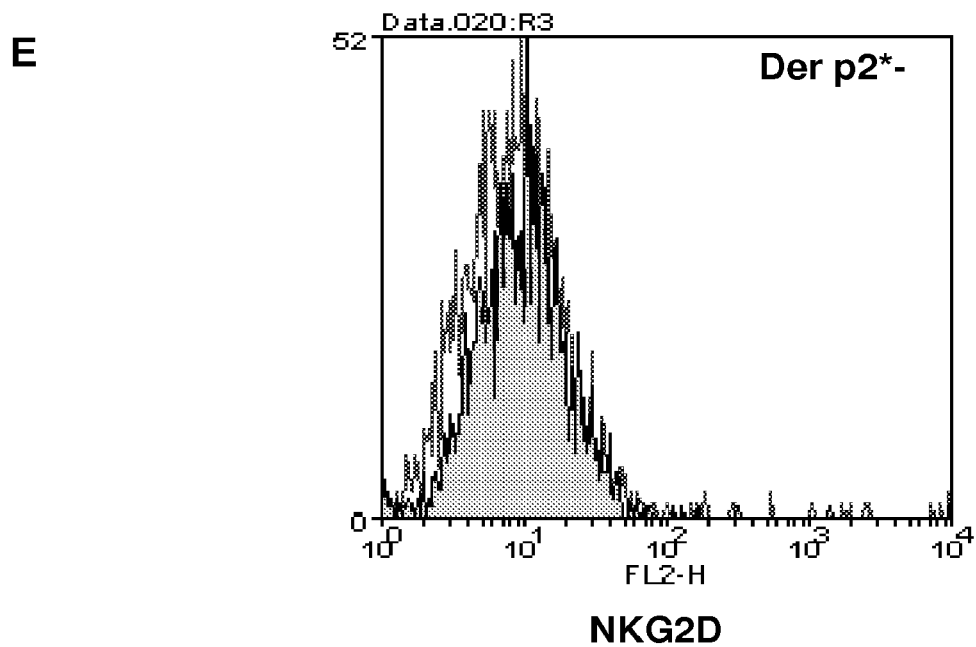
Figure 3:
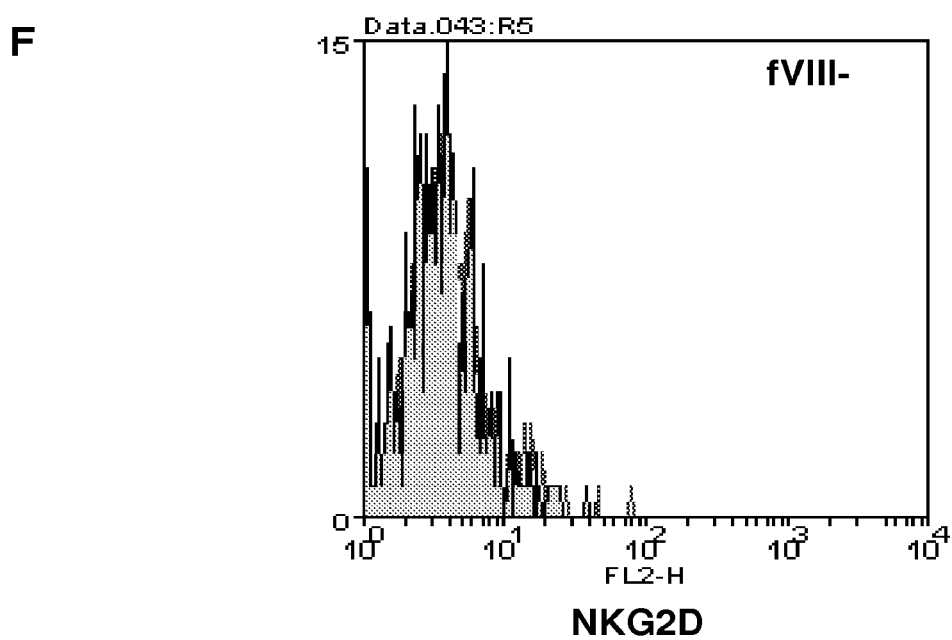
Figure 3:
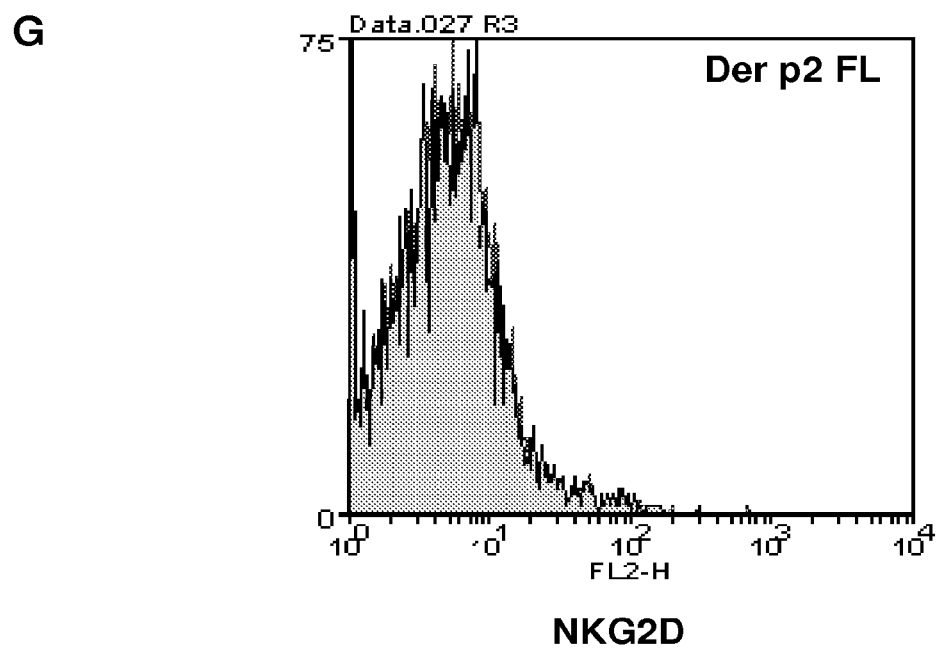

FIG. 3. Cytolytic CD4+ T cells are distinct from NK cells. See Example 5 for detailed explanation.

Figure 4:
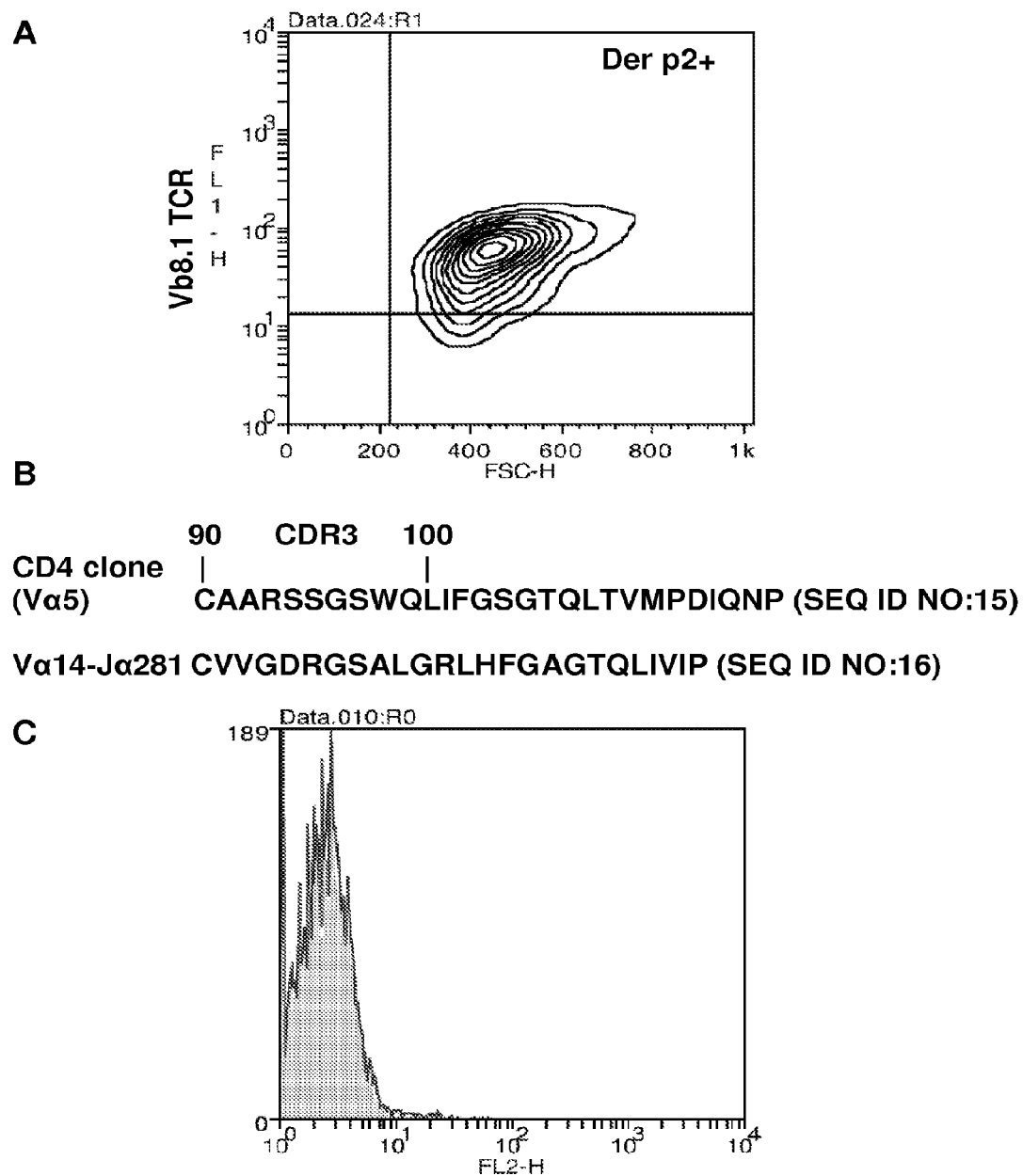

FIG. 4. Cytolytic CD4+ T cells are distinct from NKT cells. See Example 6 for detailed explanation.

Figure 5:
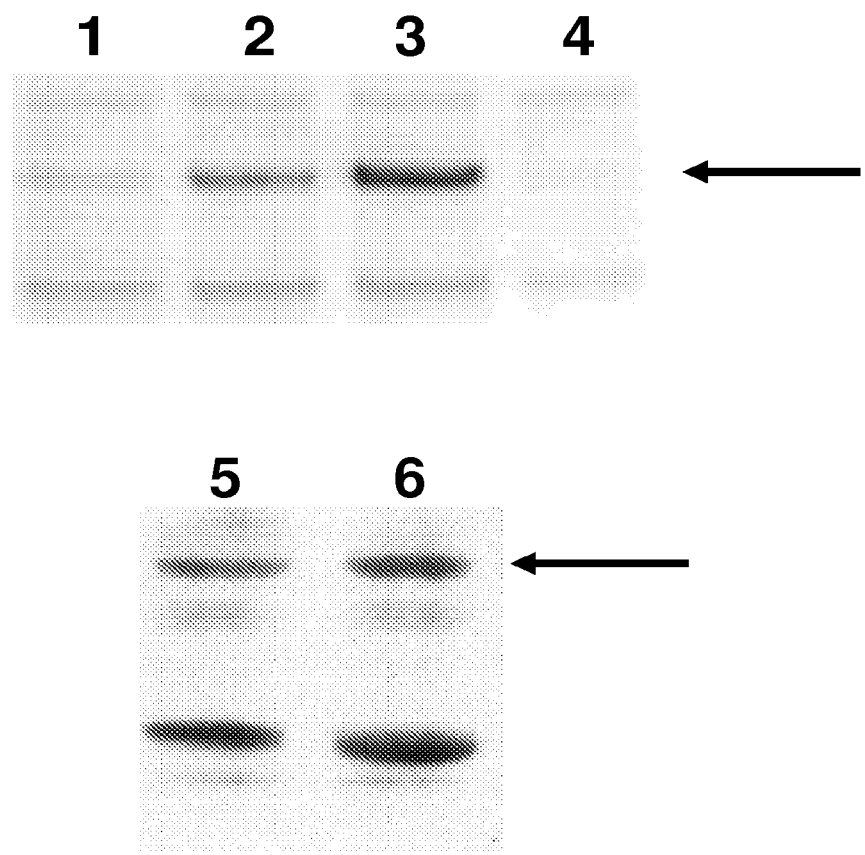

FIG. 5. Cytolytic CD4+ T cells show phosphorylation of AKT by contrast to natural CD4+ regulatory cells. See Example 7 for detailed explanation.

Figure 6:
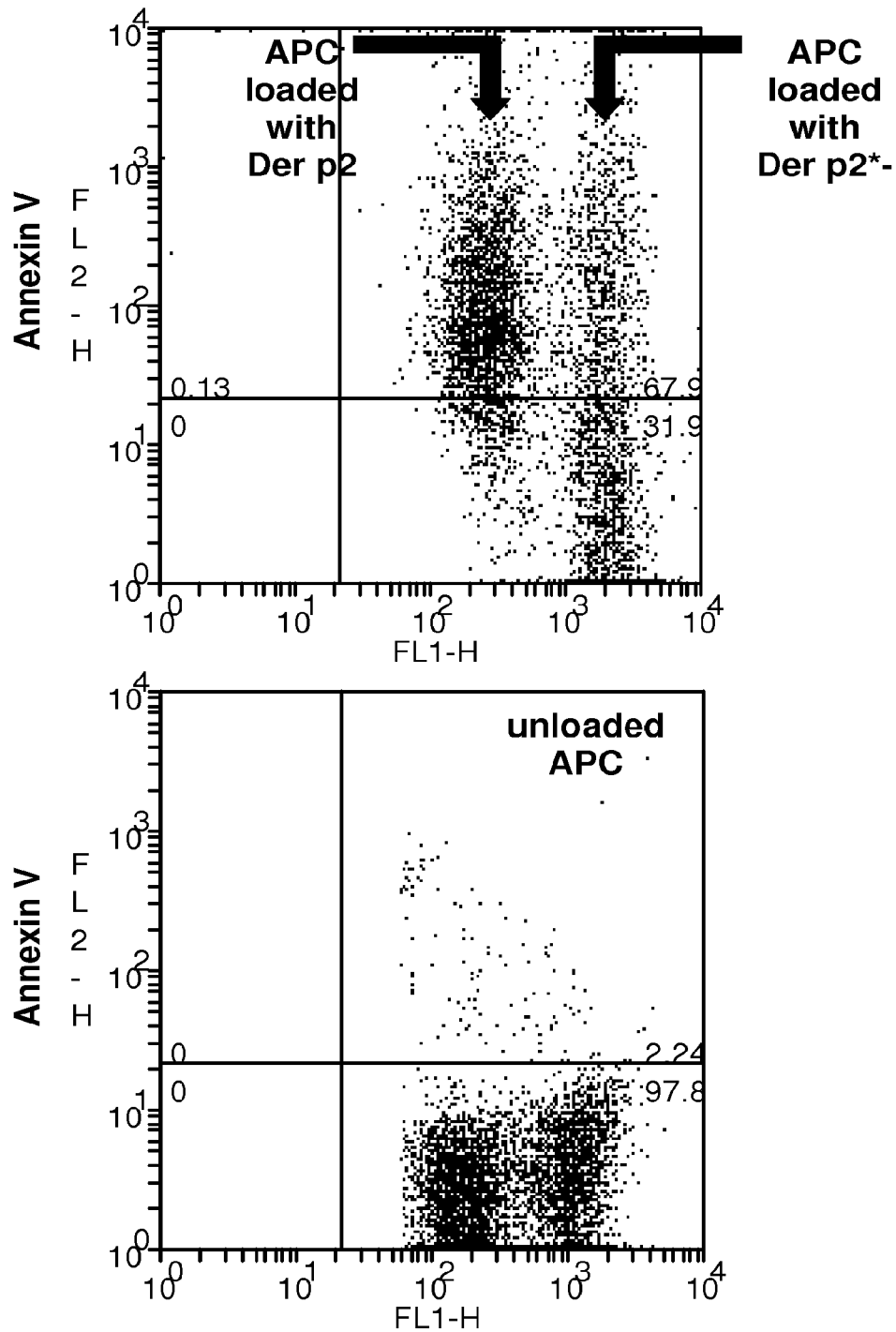
Figure 6:
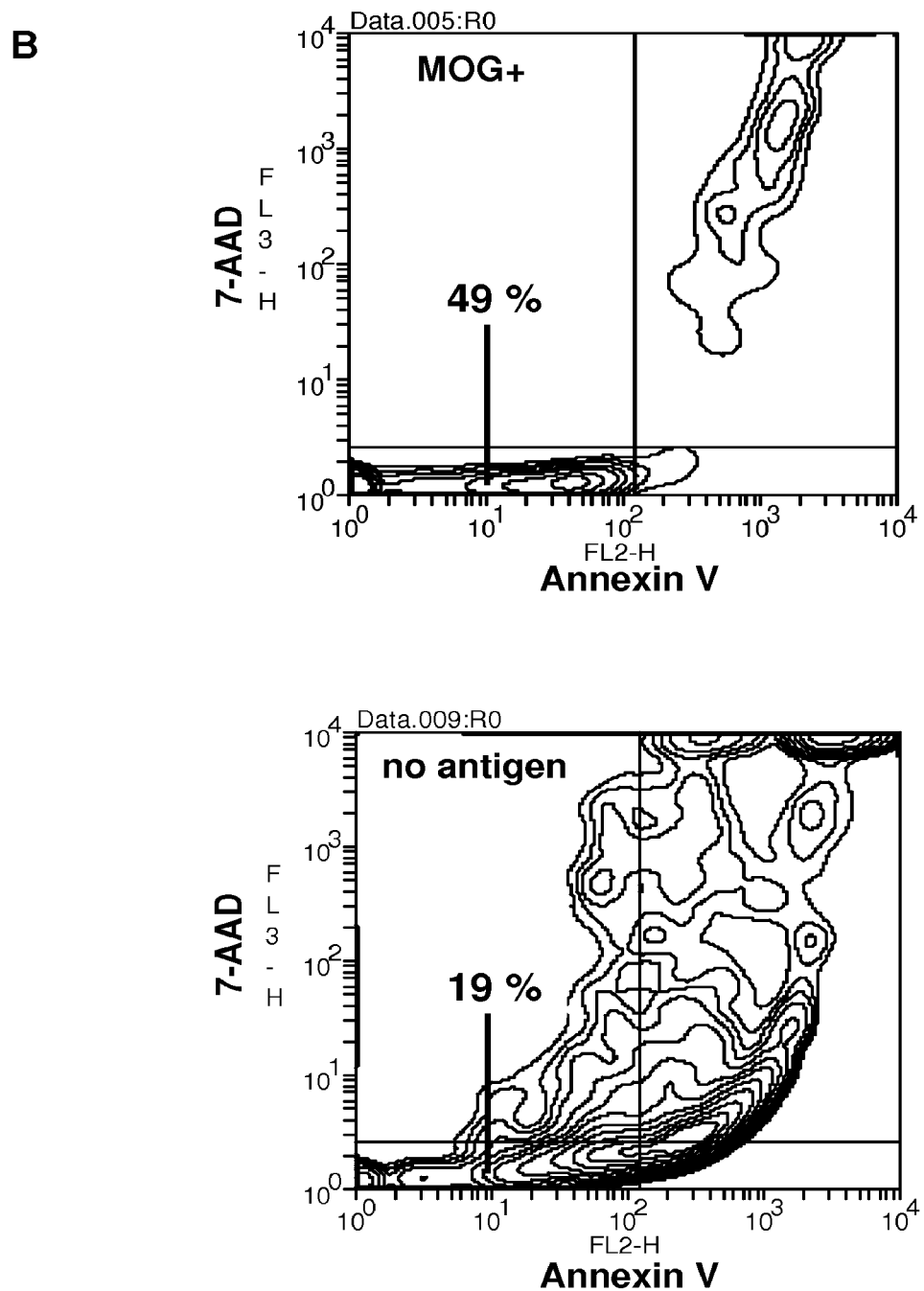
Figure 6:
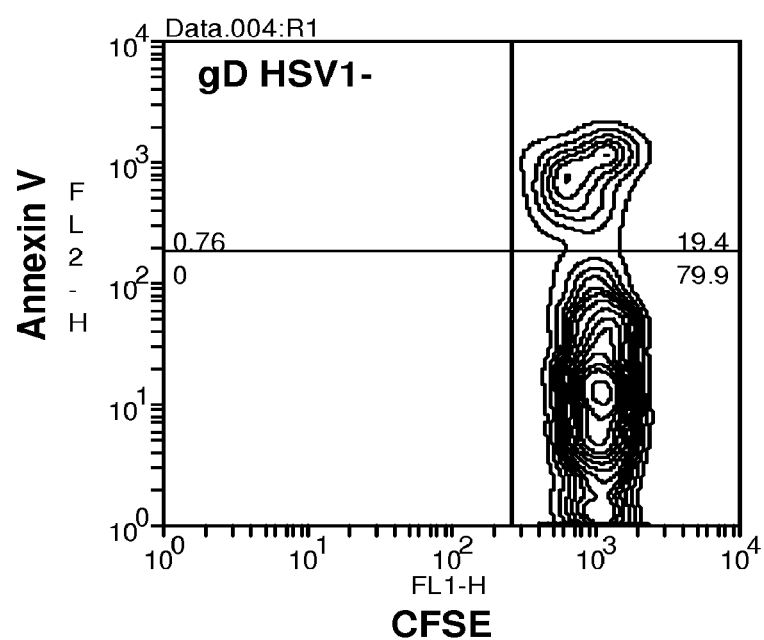
Figure 6:
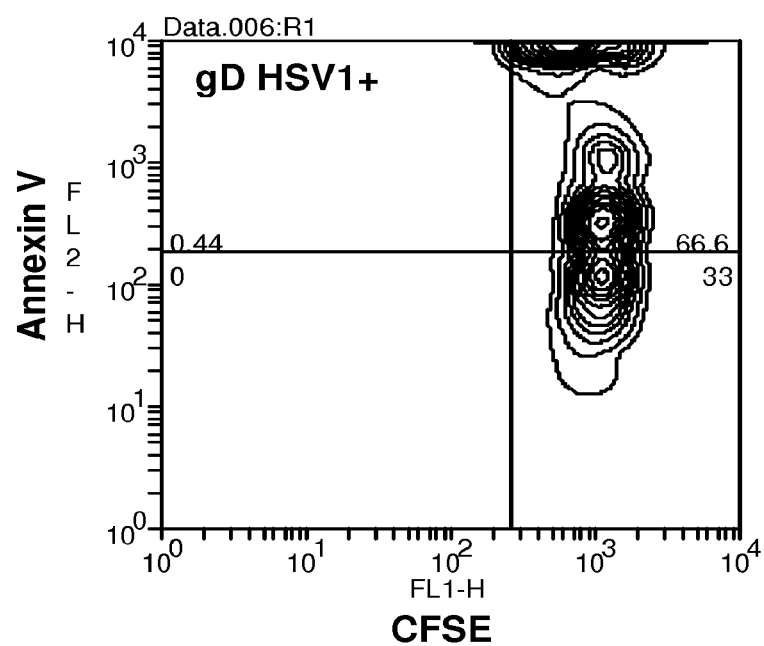

FIG. 6. Cytolytic CD4+ T cells induce apoptosis of antigen-presenting cells after cognate peptide recognition. See Example 8 for detailed explanation.

Figure 7:
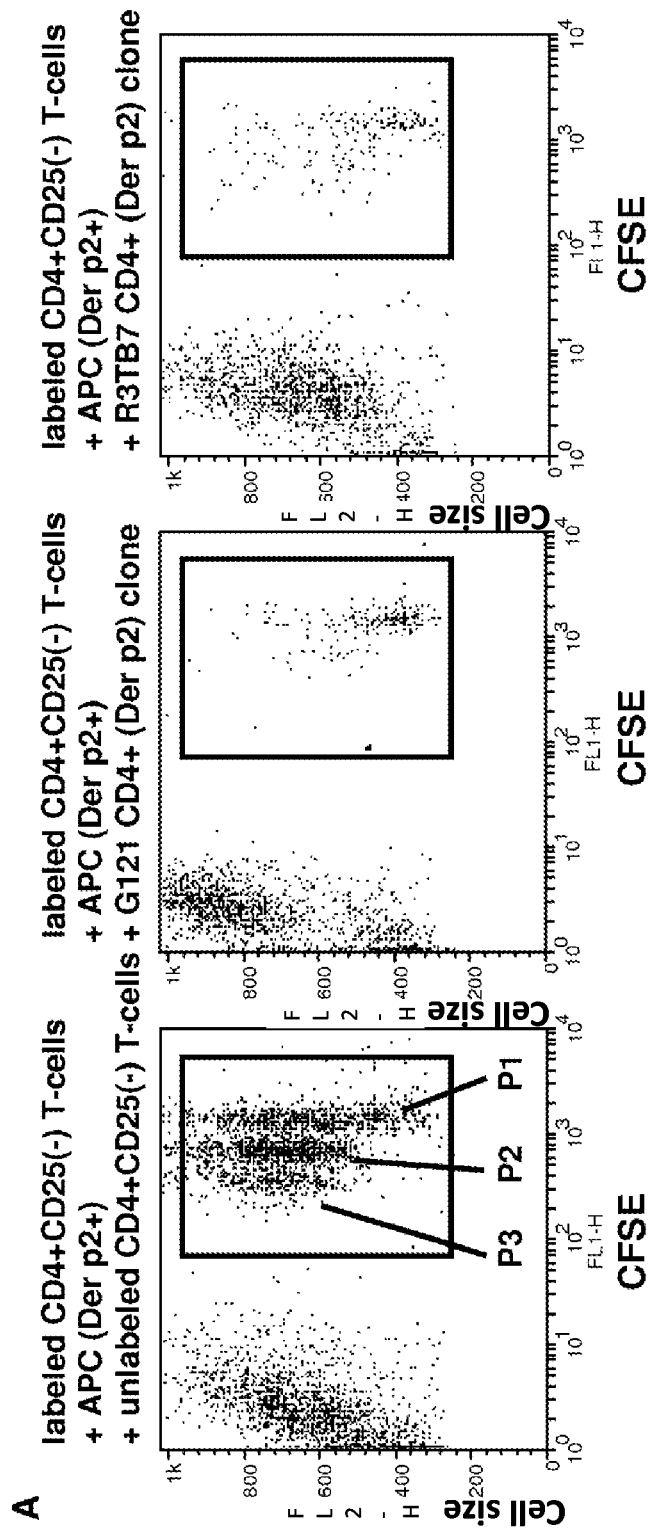
Figure 7:
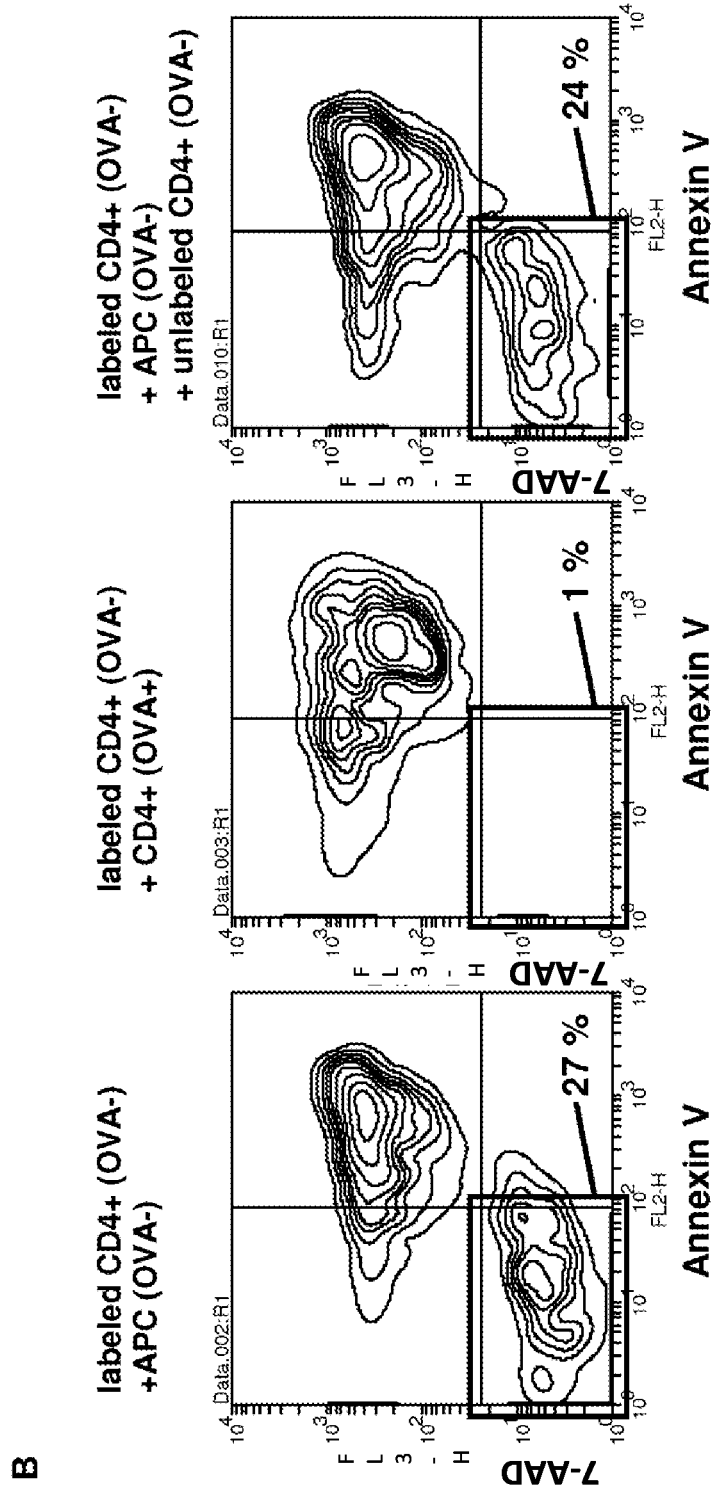

FIG. 7. Cytolytic CD4+ T cells induce apoptosis of bystander T cells. See Example 9 for detailed explanation.

DETAILED DESCRIPTION OF THE INVENTION

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein which is/are specifically recognised and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "T cell epitope" or "T-cell epitope" in the context of the present invention refers to a dominant, sub-dominant or minor T cell epitope, i.e., a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein. In particular, a T cell epitope is an epitope bound by MHC class I or MHC class II molecules.

The term "CD4+ effector cells" refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term "immune disorders" or "immune diseases" refers to diseases wherein a reaction of the immune system is responsible for or sustains a malfunction or non-physiological situation in an organism. Included in immune disorders include e.g. allergic disorders, autoimmune diseases, alloimmunisation reactions, rejection of viral vectors used in gene therapy/gene vaccination.

In the specification the following acronyms and abbreviations are used:

AKT: group of serine/protein kinases comprising AKT 1, AKT2 and AKT3 (also known as Protein Kinase B (PKB))
CD1d: Thymocyte Antigen CD1 D
CD25: Interleukin 2 Receptor, Alpha Chain (also known as IL2RA, TCGFR, and TAC antigen)
CTLA-4: Cytotoxic T-Lymphocyte Antigen 4 (also known as CD152)
CD49b: Integrin, Alpha-2 (also known as ITGA2, VLAA2)
FasL: FAS Ligand (also known as TNFSF, APT1LG1, CD95L, CD178)
Foxp3: Forkhead Box P3 (also known as SCURFIN or JM2)
GATA3: GATA-Binding Protein 3
GITR: Glucocorticoid-Induced Tnfr-Related Gene; (also known as AITR)
IFN: Interferon
NKG2D: Killer cell lectin-like receptor subfamily K, member 1, (also known as KLRK1, CD314)
T-bet: T-Box Expressed In T Cells; (also known as T-BOX 21, TBX21)
TGF-beta: Transforming Growth Factor Beta
IL: Interleukin
NK: natural killer cells
NKT: natural killer T cells

DETAILED DESCRIPTION

The present invention is based on the characterisation of a subset of CD4+ T cells having novel characteristics. This new subset of CD4+ T cells shares characteristics of regulatory T cells, of effector cells and of NK/NKT cells, but carries features and expresses properties that clearly distinguish it from regulatory cells, effector cells and NK/NKT cells. Such new CD4+ T cells are called cytolytic (or cytotoxic) CD4+ T cells (cCD4+ T cells in short). cCD4+ T cells are anergic, long-living and become activated only when recognising a cognate peptide presented by antigen-presenting cells (APCs). These cCD4+ T cells are thus strictly antigen-specific. Furthermore, they can easily be expanded (such as under ex vivo or in vitro conditions) in the presence of IL-2. An additional advantage of the cCD4+ T cells of the invention exists therein that they do not produce suppressive cytokines, which limits the risk of non-specific effects. Clearly, the advantages exhibited by the cCD4+ T cells of the invention make them excellent candidates for treating immune disorders via adoptive cell transfer.

The cCD4+ T cells of the invention are distinct from natural Tregs by absence of expression or undetectable expression of the transcription repressor Foxp3, by production of high concentrations of IFN-gamma upon stimulation with variable concentrations of IL-4, IL-5, and TNF-alpha (depending of the cytokine commitment of the corresponding effector clone), but undetectable, or no IL-17 or TGF-beta (transforming growth factor beta). In cCD4+ T-cells, IL-10 concentrations are significantly or drastically reduced or lower compared to natural CD4+ regulatory cells. Furthermore, cCD4+ T-cells according to the invention display strong phosphorylation of PI3K and AKT, and production of high concentrations of soluble FasL, though all these characteristics are not necessarily present together.

The cCD4+ T cells of the invention are distinct from CD4+ effector T cells by constitutive expression of cell surface proteins CD25, GITR and intracellular CTLA-4, but no or undetectable expression of CD28 or CD127, by cell expression of NKG2D, by production of high concentrations of soluble FasL, by co-expression of transcription factors T-bet and GATA3, by absence of IL-2 transcription, by the capacity to induce apoptosis of antigen-presenting cells (APCs), after antigenic stimulation by cognate recognition of peptides presented by MHC class II determinants and by the capacity to induce apoptosis of bystander T cells, though all these characteristics are not necessarily present together.

The cCD4+ T cells of the invention are distinct from NK cells by expression of the CD4 co-receptor, by constitutive expression of cell surface proteins CD25, GITR and intracellular CTLA-4 and by absence of (detectable) CD49b expression. NK cells do not express the CD4 co-receptor but do express CD49b The cCD4+ T cells of the invention are distinct from NKT cells by expression of an alpha-beta T cell receptor with rearranged beta chain, by absence of Valpha14 (mouse) or Valpha24 (human) TCR expression and by lack of CD1d restriction, though all these characteristics are not necessarily present together.

Hence, in one aspect, the current invention encompasses isolated populations of cytotoxic CD4+ T-cells (in either resting or activated state) characterised, when compared to natural CD4+ regulatory T-cells, by absence of expression or undetectable expression of the transcription repressor Foxp3. In a further embodiment, not excluding the previous embodiment, said population of cytotoxic CD4+ T-cells, in activated state/upon antigenic stimulation, is, compared to natural CD4+ regulatory T-cells, further characterised by strong phosphorylation of PI3K and of AKT. In a further embodiment, not excluding the previous embodiments, said population of cytotoxic CD4+ T-cells is yet further characterised by production, upon stimulation, of high concentrations of IFN-gamma with variable concentrations of IL-4, IL-5, IL-10 and TNF-alpha (depending of the cytokine commitment of the corresponding effector clone), but no or undetectable production of IL-17 or TGF-beta, all when compared to natural CD4+ regulatory T-cells. More specifically, IL-10 concentrations of activated CD4+ T-cells according to the invention are significantly and drastically reduced compared to IL-10 concentrations in activated natural CD4+ regulatory T-cells. In a further embodiment, not excluding the previous embodiments, said population of cytotoxic CD4+ T-cells is yet further characterised by production, upon antigenic stimulation, of high concentrations of soluble FasL (Fas ligand) compared to natural CD4+ regulatory T-cells.

In a further aspect, the current invention encompasses isolated populations of cytotoxic CD4+ T-cells characterised, when compared to CD4+ effector T-cells, by constitutive expression (i.e. independent of whether the cytotoxic CD4+ T-cells are at rest or activated) of cell surface proteins CD25, GITR and intracellular CTLA-4, but no or undetectable expression of CD28 or CD127. In a further embodiment, not excluding the previous embodiment, said population of cytotoxic CD4+ T-cells is, when compared to CD4+ effector T-cells, further characterised by constitutive expression of NKG2D. In a further embodiment, not excluding the previous embodiments, said population of cytotoxic CD4+ T-cells is, upon antigenic stimulation, yet further characterised by production of high concentrations of soluble FasL when compared to CD4+ effector T-cells. In a further embodiment, not excluding the previous embodiments, said population of cytotoxic CD4+ T-cells is, after antigenic stimulation, yet further characterised by co-expression of transcription factors T-bet and GATA3 when compared to CD4+ effector T-cells. In a further embodiment, not excluding the previous embodiments, said population of cytotoxic CD4+ T-cells is yet further characterised by absence of (detectable) IL-2 transcription when compared to CD4+ effector T-cells. In a further embodiment, not excluding the previous embodiments, said population of cytotoxic CD4+ T-cells is, when compared to CD4+ effector T-cells, yet further characterised by the capacity to induce apoptosis of APC, after antigenic stimulation by cognate interaction with peptide presented by MHC class II determinants. In a further embodiment, not excluding the previous embodiments, said population of cytotoxic CD4+ T-cells is, in comparison with CD4+ effector T-cells, yet further characterised by the capacity to induce apoptosis of bystander T cells.

In a further aspect, the current invention encompasses isolated populations of cytotoxic CD4+ T-cells characterised, when compared to NK-cells, by expression of the CD4 co-receptor. In a further embodiment, not excluding the previous embodiments, said population of cytotoxic CD4+ T-cells is, when compared to NK-cells, yet further characterised by absence of CD49b expression. These characteristics relative to NK-cells are independent of the activation status of the cytotoxic CD4+ T-cells and thus are detectable both in resting and activated cells.

In yet a further embodiment of the invention are comprised isolated populations of cytotoxic CD4+ T-cells characterised, when compared to NKT-cells by expression of an alpha-beta T cell receptor with re-arranged beta chain. In a further embodiment, not excluding the previous embodiments, said population of cytotoxic CD4+ T-cells is, when compared to NKT-cells, further characterised by absence of (detectable) expression of the Valpha14 (mouse) or Valpha24 (human) TCR expression. In a further embodiment, not excluding the previous embodiments, said population of cytotoxic CD4+ T-cells is, in comparison with NKT-cells, yet further characterised by lack of CD1d restriction. These characteristics relative to NKT-cells are independent of the activation status of the cytotoxic CD4+ T-cells and thus are detectable both in resting and activated cells.

The invention comprises in another aspect isolated populations of cytotoxic CD4+ T-cells displaying any possible combination of any of the characteristics as described above and relative to natural CD4+ regulatory T-cells, CD4+ effector T-cells, NK-cells and/or NKT-cells or characterised by a combination of all of these characteristics.

The CD4+ T cells of the invention can be elicited from both naïve CD4+ T cells as well as from memory CD4+ T cells, more particularly by incubation with T-cell epitopes modified by attachment of a consensus motif sequence with thioreductase activity ([CST]XX[CST]-motif, wherein [CST] is an amino acid selected from cysteine, serine and threonine, and X can be any amino acid except proline). After elicitation, they can be expanded in a suitable culture medium comprising IL-2.

The invention relates in another aspect to a method for obtaining or inducing populations of cytotoxic CD4+ T-cells as described above according to the invention, said methods comprising the steps of:
  (i) providing isolated natural naïve or memory CD4+ T-cells;
  (ii) contacting said cells with an immunogenic peptide comprising a T-cell epitope and, adjacent to said T-cell epitope or separated therefrom by a linker of at most 7 amino acids, a C-(X)2-[CST] or [CST]-(X)2-C motif; and
  (iii) expanding said cells in the presence of IL-2.

In this method the cytotoxic CD4+ T-cells can be obtained or induced in vivo or ex vivo. When in vivo, steps (i) and (iii) in the above method are redundant as the contacting of the cells with the T-cell epitope as described in (ii) is occurring by administering the T-cell epitope to the subject in need thereof, and the resulting cytotoxic CD4+ T-cells will expand in the subject's body.

The invention relates in another aspect to a method for obtaining or inducing populations of cytotoxic CD4+ T-cells as described above according to the invention, said methods comprising the steps of:

(i) administering to a subject in need thereof an immunogenic peptide comprising a T-cell epitope and, adjacent to said T-cell epitope or separated therefrom by a linker of at most 7 amino acids, a C-(X)2-[CST] or [CST]-(X) 2-C motif, thereby inducing cytotoxic CD4+ T-cells; and
(ii) isolating or obtaining the cytotoxic CD4+ T-cells induced in (i).

Alternatively, the cCD4+ T cells according to the invention may be obtained by incubation in the presence of APCs presenting the above-mentioned immunogenic peptide after transduction or transfection of the APCs with a genetic construct capable of driving expression of such immunogenic peptide. Such APCs may in fact themselves be administered to a subject in need to trigger in vivo in said subject the induction of the beneficial subset of cCD4+ T cells. In another alternative method, the cCD4+ T cells can be generated in vivo, i.e. by the administration of the above-mentioned immunogenic peptide to a subject, and collection of the cCD4+ T cells generated in vivo. Accordingly, the present invention further relates to the generation of the cCD4+ T cells of the invention both in vivo and in vitro (ex vivo) using the immunogenic peptides or APCs presenting such immunogenic peptides.

Subjects suffering from, or having an immune disorder, or whom are diagnosed to be predestined for developing an immune disorder can be treated by administering (a sufficient or effective amount of) the cCD4+ T-cells according to the invention wherein said cCD4+ T-cells are specific to a T-cell epitope relevant to the immune disorder to be treated or prevented. Prophylactic administration, treatment or prevention of immune disorders would be desirable in subjects predestined for developing an immune disorder. Such predestination may be diagnosed e.g. by a positive diagnosis of a genetic defect known to predestine a subject to develop an immune disorder or known to increase the likelihood of developing an immune disorder. Alternatively, inheritable immune disorders which have manifested themselves in one or more of the ancestors or within the family of a subject may increase the chance that/may be predestining said subject to develop the immune disorder, such subjects may therefore also be eligible for prophylactic treatment with the cCD4+ T-cells according to the invention.

The cCD4+ T cells obtainable by the above methods are of particular interest for use in the manufacture of a medicament for (prophylactically) preventing, suppressing or treating an immune disorder in a mammal. Both the use of allogeneic and autogeneic cCD4+ T-cells is envisaged. Any method comprising the administration of said cCD4+ T cells to a subject in need is known as adoptive cell therapy. As mentioned before, the cCD4+ T-cells to be included in the medicament would need to be "educated", i.e. would need to be specific, for a T-cell epitope of an antigen known to be relevant in the to be treated immune disorder.

The above-mentioned immunogenic peptides in general comprise (i) at least one T-cell epitope of an antigen of choice with a potential to trigger an immune reaction, which is coupled to (ii) an organic compound having a reducing activity, such as a thioreductase sequence motif. The antigen of choice will vary along with (and be determined by) the immune disorder to be prevented or suppressed. The T-cell epitope and the organic compound are optionally separated by a linker sequence. In further optional embodiments the immunogenic peptide additionally comprises an endosome targeting sequence (e.g. late endosomal targeting sequence) and/or additional "flanking" sequences. The immunogenic peptides can be schematically represented as A-L-B or B-L-A, wherein A represents a T-cell epitope of an antigen (self or non-self) with a potential to trigger an immune reaction, L represents a linker and B represents an organic compound having a reducing activity. The reducing activity of an organic compound can be assayed for its ability to reduce a sulfhydryl group such as in the insulin solubility assay known in the art, wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxydoreductases They exert reducing activity for disulfide bonds on proteins (such as enzymes) through redox active cysteines within conserved active domain consensus sequences: C-X(2)-C, C-X(2)-S, C-X(2)-T, S-X(2)-C, T-X(2)-C (Fomenko et al. (2003) *Biochemistry* 42, 11214-11225), in which X stands for any amino acid. Such domains are also found in larger proteins such as protein disulfide isomerase (PDI) and phosphoinositide-specific phospholipase C. In particular, the immunogenic peptides comprise as redox motif the thioreductase sequence motif [CST]-X(2)-[CST], in a further embodiment thereto, said [CST]-X(2)-[CST] motif is positioned N-terminally of the T-cell epitope. More specifically, in said redox motif at least one of the [CST] positions is occupied by a Cys; thus the motif is either [C]-X(2)-[CST] or [CST]-X(2)-[C]. In the present application such a tetrapeptide will be referred to as "the motif" or "redox motif". More in particular, the immunogenic peptides can contain the sequence motif [C]-X(2)-[CS] or [CS]-X(2)-[C]. Even more particularly, the immunogenic peptides contain the sequence motif C-X(2)-S, S-X(2)-C or C-X(2)-C.

The above immunogenic peptides can be made by chemical synthesis, which allows the incorporation of non-natural amino acids. Accordingly, in the redox motif the C representing cysteine can be replaced by another amino acids with a thiol group such as mercaptovaline, homocysteine or other natural or non-natural amino acids with a thiol function. In order to have reducing activity, the cysteines present in the motif should not occur as part of a cystine disulfide bridge. Nevertheless, the motif may comprise modified cysteines such as methylated cysteine, which is converted into cysteine with free thiol groups in vivo. The amino acid X in the [CST]-X(2)-[CST] motif of particular embodiments of the reducing compounds of the invention can be any natural amino acid, including S, C, or T or can be a non-natural amino acid. In particular, X can be an amino acid with a small side chain such as Gly, Ala, Ser or Thr. More particularly, X is not an amino acid with a bulky side chain such as Tyr; or at least one X in the [CST]-X(2)-[CST] motif can be His or Pro.

The motif in the above immunogenic peptides is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 6, 8 or 10 amino acids. Typical amino acids used in linkers are serine and threonine. Example of peptides with linkers in accordance with the present invention are CXXC-G-epitope (SEQ ID NO:17), CXXC-GG-epitope (SEQ ID NO:18), CXXC-SSS-epitope (SEQ ID NO:19), CXXC-SGSG-epitope (SEQ ID NO:20) and the like.

The immunogenic peptides can comprise additional short amino acid sequences N or C-terminally of the (artificial) sequence comprising the T cell epitope and the reducing compound (motif). Such an amino acid sequence is generally referred to herein as a 'flanking sequence'. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids.

In particular embodiments of the invention, the redox motif in the immunogenic peptide is located N-terminally from the epitope.

As detailed above, the immunogenic peptides comprise a reducing motif as described herein linked to a T cell epitope sequence. In particular cases, the T-cell epitopes are derived from proteins which do not comprise within their native natural sequence an amino acid sequence with redox properties within a sequence of 11 amino acids N- or C-terminally adjacent to the T-cell epitope of interest.

In particular embodiments, the T-cell epitope is derived from an allergen or an auto-antigen.

Allergens that can be used for selection of T-cell epitopes are typically allergens such as:
  food allergens present for example in peanuts, fish e.g. codfish, egg white, crustacea e.g. shrimp, milk e.g. cow's milk, wheat, cereals, fruits of the Rosacea family, vegetables of the Liliacea, Cruciferae, Solanaceae and Umbelliferae families, tree nuts, sesame, peanut, soybean and other legume family allergens, spices, melon, avocado, mango, fig, banana;
  house dust mites allergens obtained from *Dermatophagoides* spp or *D. pteronyssinus, D. farinae* and *D. microceras, Euroglyphus maynei* or *Blomia* sp.,
  allergens from insects present in cockroach or Hymenoptera,
  allergens from pollen, especially pollens of tree, grass and weed,
  allergens from animals, especially in cat, dog, horse and rodent,
  allergens from fungi, especially from *Aspergillus, Alternaria* or *Cladosporium*, and
  occupational allergens present in products such as latex, amylase, etc.

Auto-antigens that can be used for selection of T-cell epitopes are typically antigens such as:
  thyroglobulin, thyroid peroxidise or TSH receptor (thyroid autoimmune diseases);
  insulin (proinsulin), glutamic acid decarboxylase (GAD), tyrosine phosphatise IA-2, heat-shock protein HSP65, islet-specific glucose-6-phosphate catalytic subunit related protein (IGRP) (type 1 diabetes);
  21-OH hydroxylase (adrenalitis);
  17-alpha hydroxylase, histidine decarboxylase, Trp hydroxylase, Tyr hydroxylase (polyendocrine syndromes);
  H+/K+ ATPase intrinsic factor (gastritis & pernicious anemia);
  myelin oligodendrocyte glycoprotein (MOG), myelin basic protein (MBP), proteolipid protein (PLP) (multiple sclerosis);
  acetyl-choline receptor (myasthenia gravis);
  retinol-binding protein (RBP) (ocular diseases);
  type II (rheumatoid arthritis), type II and type IX collagen (inner ear diseases);
  tissue transglutaminase (celiac disease);
  pANCA histone H1 protein (inflammatory bowel diseases);
  heat-shock protein HSP60 (atherosclerosis);
  angiotensin receptor (arterial hypertension and pre-eclampsia)
  nitrated alpha-synuclein (Parkinson disease)

Other antigens that can be used for selection of T-cell epitopes include alloantigenic proteins derived from (present in/shed from) allografted cells or organs, soluble alloproteins (such as in administered in replacement therapy), viral vector proteins as used in gene therapy/gene vaccination, antigens derived from intracellular pathogens, and antigens derived from tumours or tumour cells.

In a further aspect, the invention encompasses a method of identifying a population of cytotoxic CD4+ T-cells, said method comprising the steps of:
  (i) providing isolated natural CD4+ T-cells such as natural CD4+ regulatory T-cells, CD4+ effector cells, NK-cells or NKT-cells;
  (ii) providing CD4+ T-cells suspected of being cytotoxic; and
  (iii) determining that the T-cells provided in (ii) display, compared to the T-cells provided in (i), the respective characteristics as described above.

In particular, the cells to be provided in step (ii) are obtainable by or may be induced or obtained by the above-described method of the invention. The cells provided in (i) are of a source such that they are not comprising cytotoxic CD4+ T-cells according to the invention. Depending on the characteristic to be determined in step (iii), the cells provided in steps (i) and/or (ii) may need to be activated by a cognate T-cell epitope; said need is derivable from the characteristics of the CD4+ T-cells of the invention as described above. The above-mentioned method of identifying a population of cytotoxic CD4+ T-cells of the invention can thus be formulated in a more extensive way as follows:
  (i) providing isolated natural CD4+ T-cells such as natural CD4+ regulatory T-cells, CD4+ effector cells, NK-cells or NKT-cells and, optionally, or when required, activating these cells;
  (ii) providing CD4+ T-cells suspected of being cytotoxic, said cells being inducible or obtainable as described above, and, optionally, or when required, activating these cells; and
  (iii) determining that the T-cells provided in (ii) display, compared to the T-cells provided in (i), the respective characteristics as described above.

Thus, in one embodiment thereto, said method is identifying cytotoxic CD4+ T-cells by determining in step (iii) the absence of or undetectable expression of the transcription receptor Foxp3 when compared with expression of Foxp3 in natural CD4+ regulatory T-cells. Said method may further comprise determining in step (iii) that the T-cells provided in (ii) display, compared to natural CD4+ regulatory T-cells provided in (i), an increased kinase activity of the serine-threonine kinase AKT. In a further embodiment, not excluding the previous embodiment, said method is further comprising determining in step (iii) that the T-cells provided in (ii) display, compared to natural CD4+ regulatory T-cells provided in (i), undetectable production of TGF-beta and undetectable or very low production of IL-10. In a further embodiment, not excluding the previous embodiments, said method is further comprising determining in step (iii) that the T-cells provided in (ii) display, compared to natural CD4+ regulatory T-cells provided in (i), high concentrations of IFN-gamma production. In a further embodiment, not excluding the previous embodiments, said method is further comprising determining in step (iii) that the T-cells provided in (ii) display, compared to natural CD4+ regulatory T-cells provided in (i), production of high concentrations of soluble FasL.

In a further embodiment, said method identifies populations of cytotoxic CD4+ T-cells according to the invention by comparing them with CD4+ effector cells. Thus, such methods may comprise determining in step (iii) that the T-cells provided in (ii) display, compared to CD4+ effector cells provided in (i), constitutive expression of Cell surface proteins CD25, GITR and intracellular CTLA-4, but not of CD28 or CD127. In a further embodiment, not excluding the previous embodiments, said method is further comprising determining in step (iii) that the T-cells provided in (ii) display, compared to CD4+ effector cells provided in (i), expression of NKG2D on the cell surface. In a further embodiment, not excluding the previous embodiments, said method is further comprising determining in step (iii) that the T-cells provided in (ii) display, compared to CD4+ effector cells provided in (i), combined expression of transcription factors T-bet and GATA3. In a further embodiment, not excluding the previous embodiments, said method is further comprising determining in step (iii) that the T-cells provided in (ii) display, compared to CD4+ effector cells provided in (i), a absence of IL-2 transcription. In a further embodiment, not excluding the previous embodiments, said method is further comprising determining in step (iii) that the T-cells provided in (ii) display, compared to CD4+ effector cells provided in (i), the capacity to induce apoptosis of APC, after antigenic stimulation by cognate interaction with peptide presented by MHC class II determinants. In a further embodiment, not excluding the previous embodiments, said method is further comprising determining in step (iii) that the T-cells provided in (ii) display, compared to CD4+ effector cells provided in (i), the capacity to induce apoptosis of bystander T cells.

In a further embodiment said method identifies populations of cytotoxic CD4+ T-cells according to the invention by comparing them with NK-cells. Thus, such methods may comprise determining in step (iii) that the T-cells provided in (ii) display, compared to NK cells provided in (i), expression of the CD4 co-receptor. In a further embodiment, not excluding the previous embodiments, said method is further comprising determining in step (iii) that the T-cells provided in (ii) display, compared to NK cells provided in (i), the absence of expression of CD49b.

In a further embodiment of the invention are included methods for identifying populations of cytotoxic CD4+ T-cells according to the invention by comparing them to NKT-cells. Such methods may comprise determining in step (iii) that the T-cells provided in (ii) display, compared to NKT-cells provided in (i), expression of an alpha-beta T cell receptor with rearranged beta chain. In a further embodiment, not excluding the previous embodiments, said method is further comprising determining in step (iii) that the T-cells provided in (ii) display, compared to NKT-cells provided in (i), absence of expression of the Valpha14 (mouse) or Valpha24 (human) TCR expression. In a further embodiment, not excluding the previous embodiments, said method is further comprising determining in step (iii) that the T-cells provided in (ii) display, compared to the NKT-cells provided in (i), absence of CD1d restriction.

In the above methods according to the invention it is further possible to identify CD4+ T-cells suspected to be cytotoxic CD4+ T-cells according to the invention as provided in step (ii) by determining in step (iii) any possible combination of any or all of the characteristics as described above and relative to natural CD4+ regulatory T-cells, CD4+ effector T-cells, NK-cells and/or NKT-cells provided in step (i), said combinations also being described above.

Accordingly, the invention provides different markers and functional properties, which can be used alone or in combination to identify and/or select and/or to use in the quality control of cCD4+ T cells. In particular embodiments the methods comprise a comparison with natural regulatory T-cells, CD4+ effector cells and NK/NKT cells. However, it is envisaged that in particular embodiments, determining the concentration of the markers mentioned above as such is sufficient to identify the cells (based upon the known expression concentrations or functional properties in natural regulatory T-cells, CD4+ effector cells and NK/NKT cells). Accordingly determining the increased activity or expression of a marker can optionally also involve determining 'high' concentrations of expression of such marker.

Generally, an enhanced activity of a kinase can be caused by an increased expression of that kinase or by phosphorylation/dephosphorylation of the kinase itself which increases its enzymatic activity. The activity of a kinase is determined by measuring directly or indirectly the amount of phosphate that is incorporated in a natural or model substrate (e.g. synthetic peptide). The activity of a kinase often depends on the phosphorylation of that same kinase. Accordingly, the degree of phosphorylation of a kinase can be indicative for its activity as is the case for AKT kinase. In the above the extent of kinase activity of the serine-threonine kinase AKT and of PI3K can be estimated via Western blotting using an antibody specific to the phosphorylated AKT or PI3K, respectively. The phosphorylation can be qualified by densitometric scanning of the Western blot. Other quantitative methods comprise methods wherein Western blots are quantified with chemoluminescence techniques (e.g. phosphorimaging) Alternatively phosphorylation can be determined quantitatively by measuring the incorporation of radioactive phosphate into a substrate. Expression of the transcription repressor Foxp3, of transcription activators T-bet and GATA3 and IL-2 expression can be estimated via Northern or RNA blotting using a labelled probe specific to the respective transcript. Expression levels can subsequently be qualified by densitometric scanning of the Northern blot. Expression levels of certain markers can alternatively be determined at the mRNA level by reverse transcriptase PCR methods. Undetectable expression as determined by RT-PCR refers to experiments wherein no signal is detected after 35 cycles of amplification.

Expression of surface markers can be evaluated using specific antibodies and a fluorescence-activated cell sorter (Facs). Facs analysis allows to determine the relative amount of cells which express a certain marker or a combination of markers. In this context, undetectable expression of a marker (for example of Foxp3), relates to a population of cells wherein less than 1%, less than 0.5% or even less than 0.1% of the cells express said marker or combination of markers.

Facs analysis is in the present invention also used to determine whether two or more markers are co-expressed. In this context two proteins are considered as co-expressed when at least 70, 80, 90, 95 or 99% of the cells in a cell population stain positive for said two or more markers in a Facs analysis.

Production of cytokines such as IL-10 and TGF-beta, IFN-gamma, IL-4, IL-5, IL-17 and IL-13, and of soluble FasL were determined in this invention via ELISA, but can also be determined via an ELISPOT assay. Cytokine concentrations are quantifiable via optical density determination in solution (ELISA) or spots indicating the presence of cytokines can be counted manually (e.g., with a dissecting microscope) or using an automated reader to capture the microwell images and to analyse spot number and size (ELISPOT). The production of cytokines as determined by ELISA is considered to be "undetectable" when the concentration is below 50 pg/ml, below 20 pg/ml or even below 10 pg/ml, and may depend from the type of antibody and the supplier). The production of cytokines as determined by ELISA is considered to be "very low" when the concentration is between 50 to 1000 pg/ml, between 100 to 1000 pg/ml, or between 200 to 1000 pg/ml. The production of cytokines as determined by ELISA is considered to be "high" when the concentration is above 1000 pg/ml, 2000 pg/ml, 5000 pg/ml or even above 7500 pg/ml.

The production of transmembrane proteins (such as FasL) as determined by ELISA is considered to be "high" when the concentration is above 50 pg/ml, 75 pg/ml, 100 pg/ml or even above 150 pg/ml.

Generally, concentration measurements refer to conditions wherein the protein production of about 100,000 cells is assayed in a volume of 200 µl.

Induction of apoptosis in APCs or bystander T cells can be measured by evaluating the binding of annexin V to phosphatidylserine exposed as the result of apoptosis.

The increase of kinase activity of the serine-threonine kinase AKT in the cytolytic or cytotoxic CD4+ regulatory T-cells of the invention is about 2-fold compared to natural CD4+ regulatory T-cells, or can be up to 3-, 4-, 5-, 5.5-, 6-, 7-, 8-, 9- or 10-fold, and can be determined by methods known in the art as explained above.

The present invention will now be illustrated by means of the following examples, which are provided without any limiting intention. Furthermore, all references described herein are explicitly included herein by reference.

EXAMPLES

Example 1

List of Peptides Used in the Examples

SEQ ID NO:1, CHGSEPCIIHRGKPF (referred to in Figures as Der p2), corresponding to amino acid sequence 21 to 35 of allergen Der p 2 and containing a T cell epitope and a natural thioreductase sequence (underlined).

SEQ ID NO:2, CGPCGGYRSPFSRVVHLYRNGK (referred to in Figures as MOG-F), corresponding to amino acid sequence 40-55 derived from the myelin oligodendrocytic glycoprotein (MOG) and modified by addition of a thioreductase motif (underlined) separated from the first MHC class II anchoring residue by a Gly-Gly sequence.

SEQ ID NO:3, CGPCGGYVPFHIQVP (referred to in Figures as LP HAdV5), corresponding to amino acid sequence 555-563 from Late Protein 2 (hexon protein family) derived from human adenovirus 5 (HAdV-5) and modified by addition of a thioreductase motif (underlined) separated from the first MHC class II anchoring residue by a Gly-Gly sequence.

SEQ ID NO:4, CGHCGGAAHAEINEAGR (referred to in Figures as OVA+), corresponding to amino acid sequence 330-340 derived from chicken ovalbumin and modified by addition of a thioreductase motif (underlined) separated from the first MHC class II anchoring residue by a Gly-Gly sequence.

SEQ ID NO:5, CHGCGGEPCIIHRGKPF (referred to in Figures as Der p2+), corresponding to amino acid sequence 25 to 35 of allergen Der p 2 and modified by addition of a thioreductase motif (underlined) separated from the first MHC class II anchoring residue by a Gly-Gly sequence.

SEQ ID NO:6, YRSPFSRVVHLYRNGK (referred to in Figures as MOG-), corresponding to amino acid sequence 40-55 derived from the myelin oligodendrocytic glycoprotein (MOG).

SEQ ID NO:7, IIARYIRLHPTHYSIRST (referred to in Figures as fVIII-), corresponding to amino acid sequence 2144-2161 derived from the C1 domain of human Factor VIII.

SEQ ID NO:8, CGFSSNYCQIYPPNANKIR (referred to in Figures as Der p1+), corresponding to amino acid sequence 114 to 128 of allergen Der p 1 and modified by addition of a thioreductase motif (underlined) to the amino-terminal part of the first MHC class II anchoring residue.

SEQ ID NO:9, NACHYMKCPLVKGQQ (referred to in Figures as Der p2*-), corresponding to amino acid sequence 71 to 85 of allergen Der p 2.

SEQ ID NO:10, CHGAEPCIIHRGKPF (referred to in Figures as Der p2mut), corresponding to peptide of SEQ ID1 containing a single S to A mutation (underlined) that abolishes the thioreductase activity of peptide.

SEQ ID NO:11, TYLRLVKIN (referred to in Figures as gD HSV1-), corresponding to amino acid sequence 188 to 196 derived from glycoprotein D of human herpesvirus 1.

SEQ ID NO:12, CGHCTYLRLVKIN (referred to in Figures as gD HSV1+), corresponding to amino acid sequence 188 to 196 derived from glycoprotein D of human herpesvirus 1 and modified by addition of a thioreductase motif (underlined) to the amino-terminal part of the first MHC class II anchoring residue.

SEQ ID NO:13, SNYCQIYPPNANKIR (referred to in Figures as Der p1-), corresponding to amino acid sequence 114 to 128 of allergen Der p 1.

SEQ ID NO:14, ISQAVHAAHAEINEAGR (referred to in Figures as OVA-) corresponding to amino acid sequence 324-340 derived from chicken ovalbumin.

Example 2

Cytolytic CD4+ T Cell Clones Express Markers Associated with Regulatory T Cells

The phenotype of natural regulatory T cells is characterised by high expression of CD25 at rest, together with high expression of intracellular CTLA-4 and surface GITR (Glucocorticoid-Induced TNF receptor), which distinguish regulatory T cells form effector cells.

Peptides derived from 4 distinct antigens were used: an allergen, an autoantigen and a virus-derived surface antigen and a common antigen.

CD4+ T cells were obtained from the spleen of BALB/c mice immunised with peptide p21-35 (SEQ ID NO:1, CHG-SEPCIIHRGKPF), followed by purification by magnetic beads sorting. A T cell clone was obtained by in vitro stimulation with peptide-loaded APCs (loaded with peptide of SEQ ID NO:1). The clonal cells were analysed on day 15 after stimulation by fluorescence-activated cell sorting (Facs) using a FACSCalibur© flow cytometer. CD4+ T cells were stained with an antibody recognising CD25, then permeabilised with saponin before incubation with an antibody specific for CTLA-4. Data show strong positivity for both CD25 and CTLA-4 (FIG. 1A). The T cell clone was also tested for expression of GITR and CD28, showing a strong positivity for GITR (FIG. 1D), but absence of CD28 (FIG. 1F). A CD4+ T cell clone obtained after mouse immunisation with peptide of SEQ ID NO:2 (CGPCGGYRSPFSRVVHLYRNGK) was tested for the expression of CD25 (FIG. 1B) and CD28 (FIG. 1G), showing strong CD25 expression but absence of CD28. Further, CD25 expression (FIG. 1O) or absence of CD28 expression (FIG. 1H) was shown for a clone obtained after immunisation with peptide of SEQ ID NO:3 (CGPCG-GYVPFHIQVP). Expression of surface GITR, an hallmark of the 3 clones shown above was also observed with a CD4 T cell clone specific for peptide of SEQ ID NO:4 (CGHCG-GAAHAEINEAGR), FIG. 1E.

Example 3

Cytolytic CD4+ T Cell Clones Co-Express Transcription Factors T-Bet and GATA3 but not Foxp3

T-bet is considered as a marker for Th1 cells and GATA3 as a marker for Th2 cells. In helper cells, expression of T-bet excludes expression of GATA3 and vice-versa.

A T cell clone was obtained as described in Example 2 with a peptide of SEQ ID NO:1. After antigenic stimulation, cells were fixed and permeabilised before intracellular staining with specific antibodies to either Foxp3, T-bet or GATA3 and analysed by Facs as described in Example 2. Cells are shown to be positive for both T-bet and GATA3 but not for Foxp3 (FIG. 2A). Dual staining with T-bet and GATA-3 of a T cell clone obtained by immunisation with peptide of SEQ ID NO:4 (FIG. 2B, upper panel) of by peptide of SEQ ID NO:2 (FIG. 2C, lower panel) is also shown.

Example 4

Cytolytic CD4+ T Cell Clones Produce Soluble FasL and IFN-Gamma

The profile of cytokines produced by effector cells characterises the subset to which cells belong. Th1 cells produce IL-2, IFN-gamma and TNF-alpha, Th2 cells produce IL-4, IL-5, IL-13 and IL-10, and Th17 cells produce IL-17 and IL-6.

Two distinct T cell clones were obtained from 2 mice immunised with a peptide containing a thioreductase motif (SEQ ID NO:5, CHGCGGEPCIIHRGKPF).

In addition, T cell lines were obtained from mice immunised with a T cell epitope in natural sequence (SEQ ID NO:6, YRSPFSRVVHLYRNGK) derived from the myelin oligodendrocytic glycoprotein (MOG) and were stimulated in vitro in the presence of the same T cell epitope modified by addition of a thioreductase motif (underlined) separated from the first MHC class II anchoring residue by a Gly-Gly sequence (SEQ ID NO:2, CGPCGGYRSPFSRVVH-LYRNGK).

The two CD4 T cell clones specific for SEQ ID NO:5 and a CD4 T cell line specific to SEQ ID NO:6 were stimulated with peptides for 48 h and the supernatants were assessed for the presence of cytokines and of FasL using ELISAs with specific antibodies. Table 1 shows that the two CD4 T cell clones obtained from immunisation with peptide of SEQ ID NO:5 and the CD4 T cell clone obtained with the natural sequence SEQ ID NO:6, when stimulated in vitro with either peptide of SEQ ID NO:5 for the first two clones or peptide of SEQ ID NO:2 for the third clone, significant amounts of soluble FAS-L was detected in the supernatants. By comparison, the T cell clone obtained by immunization with peptide of SEQ ID NO:6 was stimulated in vitro with the same peptide, no FAS-L was detected. An additional control is shown, made from a T cell clone stimulated by peptide of SEQ ID NO:7 (IIARYIRLHPTHYSIRST, a T cell epitope derived from human Factor VIII), which does not contain a thioreductase motif.

TABLE 1

| T cell Specificity | sFAS-L (pg/ml) |
|---|---|
| cCD4 T (R3TB7) to SEQ ID NO: 5 | 115.1 |
| cCD4 T (22N) to SEQ ID NO: 5 | 176.1 |
| cCD4 T to SEQ ID NO: 2 | 50.8 |
| CD4 T to SEQ ID NO: 6 | ND |
| CD4 T (p352a) to SEQ ID NO: 7 | ND |

A consistent finding with all clones obtained by immunisation with peptides containing a thioreductase motif, or effector CD4 T cells stimulated in vitro with peptides containing a thioreductase motif, was the sustained production of IFN-gamma, while IL-2, TGF-beta and IL-17 were not detected (ND). Low concentrations of IL-4, IL-5 and IL-10 could be detected, which correlated with the cytokine profile of the corresponding effector cell (Table 2).

TABLE 2

|  | TGF-β | IL-17 | IFN-γ | IL-5 | IL-4 | IL-10 | IL-2 |
|---|---|---|---|---|---|---|---|
| cCD4 T (R3TB7) to SEQ ID NO: 5 | ND | ND | 4151 | 8 | ND | ND | ND |
| cCD4 T (22N) to SEQ ID NO: 5 | ND | ND | 9139 | 2 | ND | 102 | ND |
| cCD4 T to SEQ ID NO: 2 | ND | ND | 133 | 16 | ND | ND | ND |
| CD4 T to SEQ ID NO: 6 | ND | ND | 4652 | 2538 | 42 | 5001 | 7 |
| CD4 T (p352a) to SEQ ID NO: 7 | ND | ND | 131 | 725 | 252 | 3847 | 19 | cytokine concentrations are expressed as pg/ml

Example 5

Cytolytic CD4+ T Cells are Distinct from NK Cells

NK cells are characterised by expression of CD49b and NKG2D but not CD4.

T cell clones were obtained from mice immunised with peptides of SEQ ID NO:5 or of SEQ ID NO:4. Such clones were analysed by fluorescence-activated cell sorting for the expression of CD49b cell marker on day 14 after in vitro restimulation. Antibodies specific to CD49b (DX5 antibody) were used in the FACS analysis.

The results indicated that the two clones (FIG. 3A and FIG. 3B, respectively) were uniformly negative for CD49b, thereby distinguishing cytolytic T cell clones from NK cells.

FIGS. 3C and 3D show the expression of NKG2D on cytolytic CD4 cells obtained from mice immunised with peptide of SEQ ID NO:5 or peptide of SEQ ID NO:8 (CGFSS-NYCQIYPPNANKIR), respectively.

By comparison, expression of NKG2D was evaluated on effector CD4 T cell clones obtained by immunisation by peptide of SEQ ID NO:9 (NACHYMKCPLVKGQQ) or of SEQ ID NO:7, containing no thioreductase motif (FIGS. 3E and 3F, respectively) and effector CD4 T cells obtained by immunisation with a full allergen, Der p2 (FIG. 3G, denoted in FIG. 3G as Der p2 FL). None of these non-cytolytic effector CD4 T cells expressed NKG2D.

Example 6

Cytolytic CD4+ T Cells are Distinct from NKT Cells

NKT cells carry an invariant alpha chain (Valpha14-Jalpha281 in the mouse, Valpha24-JQ in man) and variable but not rearranged beta chain at the TCR level. In addition, NKT cells produce high concentrations of IL-4, and most NKT cells are restricted by the CD1d molecule. CD1d restriction refers to the fact that the recognition of an antigen loaded by CD1d+ cell (antigen presenting cell) is mediated through the recognition of the antigen by a T cell when such antigen is presented by the CD1d molecule. In the present example the antigen presenting cell is replaced by a soluble from of CD1d (BD™ DimerX; Becton Dickinson)

A T cell clone obtained as in Example 5 by stimulation with peptide of SEQ ID NO:5 was assessed on day 14 after restimulation. Table 2 shows that such clone (R3TB7) does not produce detectable concentrations of IL-4, distinguishing this clone from NKT cells. Cells were further analysed by Facs using specific antibodies to the Vbeta8-1 TCR (FIG. 4A). In addition, the sequence of the alpha chain of the TCR was obtained by PCR. The results indicate that the clone expressed a rearranged Vbeta chain and a Valpha sequence belonging to the Valpha5 subfamily (and not the sequence of the invariant Valpha14-Jalpha281 TCR chain), thereby distinguishing the cytolytic CD4+ T cells (R3TB7) from NKT cells (FIG. 4B). The T cell clone was further tested for staining with peptide of SEQ ID NO:5-loaded CD1d-Ig molecule (BD™ DimerX; Becton Dickinson) and analysed by Facs. This experiment shows that either the antigenic peptide is not loaded on soluble CD1d and or that the cCD4+ Tcell is not equipped with the appropriate receptor to recognize the peptide as associated with the CD1d molecule.

The results indicate that the cytolytic CD4+ cells were not restricted by CD1d molecule, further distinguishing them from CD4+NKT cells (FIG. 4C). Data is representative of different clones with distinct antigen specificity.

Example 7

Cytolytic CD4+ T Cells Show Phosphorylation of AKT by Contrast to Natural CD4+ Regulatory Cells In CD4 T lymphocytes the phosphorylation of Ser473 of serine-threonine kinase AKT is indicative of its activity. To show that AKT kinase activity was present and/or increased when CD4+ T cells were incubated with peptides containing a thioreductase motif, we made use of peptide of SEQ ID NO:5 (containing such a motif) and peptide of SEQ ID NO:10 (CHGAEPCIIHRGKPF, containing a single S to A mutation (underlined) that abolishes the thioreductase activity of peptide of SEQ ID NO:1).

The cytolytic CD4+ T cell clone R3TB7 was obtained by immunisation with peptide of SEQ ID NO:1, followed by cloning, and amplification in the presence of dendritic cells presenting the same peptide. The R3TB7 CD4+ T cell clone was incubated for 30 minutes with antigen-presenting cells (dendritic cells) without peptide (FIG. 5, lane 1), with APC preloaded with redox-inactive peptide of SEQ ID NO:10 (FIG. 5, lane 2), or with APC preloaded with a redox active peptide of SEQ ID NO:5 (FIG. 5, lane 3). Cells were then lysed and an aliquot was run on SDS-PAGE, the proteins were then transferred to a PVDF membrane and probed for the phosphorylated form of AKT (Ser473) using a specific antibody. A control containing no T cells was also included (lane 4). The resulting phosphorylation of the serine-threonine kinase AKT in CD4+ T-cells incubated with redox-active peptide of SEQ ID NO:5 was 5.5-fold higher as compared to AKT in the same CD4+ T-cells incubated without unloaded APCs (FIG. 5, lane 1, mimicking natural CD4+ regulatory T-cells), and 2-fold higher compared to AKT in the same CD4+ T-cells incubated with the redox-inactive peptide of SEQ ID NO:10.

Thus, a CD4+ T cell clone obtained from animals immunised with a thioreductase containing peptide shows strong kinase activity of AKT when incubated in vitro with a peptide containing a thioreductase activity (peptide of SEQ ID NO:5), yet maintains AKT kinase activity when incubated with a peptide from which the thioreductase activity has been removed by mutation (peptide of SEQ ID NO:10), illustrating the stable commitment of such T cell clone under in vitro stimulation conditions. These results as illustrated were obtained after a single incubation of cells with peptides. This unexpected observation contrasts with the results disclosed by Crellin et al. (2007) (*Blood* 109, 2014-2022) showing a decreased kinase activity of AKT to be associated with natural CD4+ regulatory T-cells, and emphasises the difference between the cytolytic CD4+ T-cells with suppressive properties of the invention and natural CD4+ regulatory T-cells.

To determine whether naïve CD4+ T cells showed increased AKT kinase activity when incubated in vitro with peptides containing a thioreductase motif, we purified CD4 T cells from splenocytes of naïve C57BL/6 mice expressing a TCR transgene specific for peptide of SEQ ID NO:6. Cells were stimulated once for 15 minutes with T cell depleted splenocytes preloaded with peptide of SEQ ID NO:6 (FIG. 5, lane 5) containing no thioreductase motif, or with peptide of SEQ ID NO:2 (FIG. 5, lane 6) containing a thioreductase motif. Cell lysis and SDS-PAGE electrophoresis were carried out as described above. The membrane was probed with the antibody recognising activated AKT (Ser473). Densitometric analysis showed that phosphorylation of AKT was 30% higher when naïve cells were stimulated with peptide of SEQ ID NO:2 than phosphorylation obtained with peptide of SEQ ID NO:6. Thus, a single incubation of naïve CD4 T cells with a peptide containing a thioreductase motif is sufficient to elicit significantly higher kinase activity of AKT than observed with cells incubated with the same peptide but with no thioreductase motif.

Example 8

Cytolytic CD4+ T Cells Induce Apoptosis of Antigen-Presenting Cells after Cognate Peptide Recognition Two distinct populations of APCs (WEHI cells) were loaded for 1 hr with either peptide of SEQ ID NO:1 or with peptide of SEQ ID NO:9. The cells loaded with peptide of SEQ ID NO:1 were labelled with 80 nM CFSE; those loaded with peptide of SEQ ID NO:9 were labelled with 300 nM CFSE. The two APC populations could therewith be distinguished from each other. CFSE is a label for cytoplasmic proteins enabling the follow-up of cell divisions based on staining intensity, which is reduced by 50% after every cell division, but also the identification of a cell population within complex mixtures of cells in culture. CFSE-labelled cells were mixed and subsequently incubated for 18 hrs with a cytolytic CD4 T cell clone (G121) obtained by immunisation with peptide of SEQ ID NO:1. Peptide p71-85 (SEQ ID NO:9, Der p2*-) represents an alternative major T-cell epitope derived from Der p 2 but does not comprise a thioreductase-active motif. Apoptosis of CFSE-labelled APCs was measured by the binding of annexin V. WEHI cells presenting p21-35 were fully lysed, whereas only about 40% of p71-85

(SEQ ID NO:1, Der p2)-loaded cells were affected. As a control, unloaded APCs were used. Results are depicted in FIG. 6A.

FIG. 6B shows that splenic B cells from naïve C57BL/6 mice were induced into apoptosis when cultured for 18 hrs with a cytolytic CD4 T cell clone obtained from mice immunised with peptide of SEQ ID NO:2, as shown by dual staining with annexin V and 7-AAD (FIG. 6B, lower panel) but not when the antigen was absent (FIG. 6B, upper panel).

FIG. 6C shows the killing of CFSE-stained WEHI B cells loaded with peptide of SEQ ID NO:11 (TYLRLVKIN, a T epitope derived from the HSV-1 virus) and co-cultured for 18 hrs with a cell line obtained from mice immunised with peptide of SEQ ID NO:12 (CGHCTYLRLVKIN), which comprises a thioreductase motif. More than 65% of the WEHI cells were stained positive for Annexin V (FIG. 6C, lower panel), as opposed to background staining (19%) obtained when a control T cell line derived from mice immunised with a peptide of SEQ ID NO:11 was used (FIG. 6C, upper panel).

Example 9

Cytolytic CD4+ T Cells Induce Apoptosis of Bystander T Cells

The mechanism of bystander T cell suppression was examined with polyclonal CD4+CD25(−) T cells and with various CD4+ effector T cell clones.

The capacity of cytolytic CD4+ T cells to suppress the proliferation of CFSE labelled CD4+CD25(−) T cells activated by incubation with an antibody to CD3 in the presence of antigen-presenting cells was assayed. Two cytolytic CD4+ T cell clones elicited by immunisation with peptide of SEQ ID NO:1 (G121 and R3TB7, respectively; indicated in FIG. 7A as "CD4+ (Der p2) clone") were used. The APCs were loaded with peptide of SEQ ID NO:5 (indicated in FIG. 7A as "APC (Der p 2+)"). The number of detectable CD4+CD25(−) T cells (frames), as well as the number of observed divisions dramatically dropped within 48 h incubation when either one of the two cytolytic clones were added (FIG. 7A, middle and right panels). Interestingly, only activated CD4+CD25(−) T cells were lysed. The control experiment in which the cytolytic CD4+ T-cells were replaced by an identical number of unlabeled CD4+CD25(−) T cells eliminated a possible artefact related to variable numbers of total cells in the culture medium (FIG. 7A, left panel). P1 to P3 in the Figure depict the decrease in CFSE labelling as a function of the number of cell divisions.

An effector CD4+ T cell clone obtained from BALB/c mice immunised with a major epitope from the allergen Der p1 (SNYCQIYPPNANKIR, SEQ ID NO:13) was labelled with CFSE and incubated with APC loaded with the same peptide (114-128). When an identical number of unlabelled effector cells was added, a 40% baseline mortality of the CFSE-labelled cells was observed. When co-cultured with a cytolytic CD4 cell clone obtained from mice immunised with peptide of SEQ ID NO:8, more than 73% of the effector T cells died.

Similar results were obtained when a CD4 T cell line obtained from mice immunised with natural epitope from ovalbumin (ISQAVHAAHAEINEAGR, SEQ ID NO:14) was used as a bystander target for apoptosis. The cell line was labelled with CFSE (denoted in FIG. 7B as "labelled CD4+ (OVA−)") and cultured with peptide of SEQ ID NO:14-loaded splenic APC (denoted in FIG. 7B as "APC (OVA−)") followed by staining with apoptosis markers annexin V and 7-AAD.

FIG. 7B shows that 27% or 24% of the bystander CD4 cells were alive (annexin V and 7-AAD negative) when cultured with APC alone (left panel) or with APC and the same unlabelled CD4 T cell line (denoted in FIG. 7B as "unlabeled CD4+ (OVA−)"; right panel of FIG. 7B), respectively. When co-cultured with a T cell line derived from mice immunised with the ovalbumin peptide comprising a thioreductase motif (SEQ ID NO:4; cell line denoted in FIG. 7B as "CD4+ (OVA+)"), less than 1% of the labelled bystander cells were detected within the double-negative region corresponding to living cells.

I claim:

1. A method of identifying a population of cytolytic CD4+ T-cells, said method comprising the steps of:
   (i) providing isolated natural CD4+ regulatory T-cells;
   (ii) providing isolated CD4+ T cells suspected of being cytolytic; wherein the CD4+ T cells suspected of being cytolytic are obtained by a method comprising contacting natural naive or memory CD4+ T cells with an immunogenic peptide comprising an MHC class II T cell epitope and adjacent to said T cell epitope or separated therefrom by at most 7 amino acids a C-(X)2-[CST] or [CST]-(X)2-C motif,
   or wherein the CD4+ T cells suspected of being cytolytic are obtained by a method comprising administering an immunogenic peptide comprising an MHC class II T cell epitope and adjacent to said T cell epitope or separated therefrom by at most 7 amino acids a C-(X)2-[CST] or [CST]-(X)2-C motif to a subject, and collecting of CD4+ T cells generated in vivo from said subject; and
   (iii) measuring that the CD4+ T-cells suspected of being cytolytic provided in (ii) display, compared to the isolated natural CD4+ regulatory T-cells provided in (i), undetectable expression of the transcription repressor Foxp3, and increased activity of serine-threonine kinase AKT.

2. The method according to claim 1, said method further comprising determining in step (iii) that the T-cells provided in (ii) display, compared to the T-cells provided in (i), undetectable production of TGF-beta and undetectable or very low production of IL-10.

3. The method according to claim 1, said method further comprising determining in step (iii) that the T-cells provided in (ii) display, compared to the T-cells provided in (i), production of high concentrations of IFN-gamma.

4. The method according to claim 1, said method further comprising determining in step (iii) that the T-cells provided in (ii) display, compared to the T-cells provided in (i), production of high concentrations of soluble Fas ligand (FasL).

5. A method of identifying a population of cytolytic CD4+ T-cells, said method comprising the steps of:
   (i) providing isolated natural CD4+ regulatory T-cells;
   (ii) providing isolated natural naïve or memory CD4+ T-cells;
   (iii) contacting said isolated natural naïve or memory CD4+ T-cells with an immunogenic peptide comprising a T-cell epitope and, adjacent to said T-cell epitope or separated therefrom by a linker of at most 7 amino acids, a C-(X)2-[CST] or [CST]-(X)2-C motif; and
   (iv) measuring that the cells obtained in step (iii) display, compared to the isolated natural CD4+ regulatory T-cells provided in (i), undetectable expression of the transcription repressor Foxp3, and an increased activity of serine-threonine kinase AKT.

6. A method of identifying a population of cytolytic CD4+ T-cells, said method comprising the steps of:
   (i) providing isolated natural CD4+ regulatory T-cells;
   (ii) providing isolated CD4+ T-cells suspected of being cytolytic, wherein the CD4+ T cells suspected of being cytolytic are obtained by a method comprising administering an immunogenic peptide comprising an MHC class II T cell epitope and adjacent to said T cell epitope or separated therefrom by at most 7 amino acids a C-(X)2-[CST] or [CST]-(X)2-C motif to a subject, and collecting of CD4+ T cells generated in vivo from said subject; and
   (iii) measuring that the CD4+ T-cells suspected of being cytolytic provided in (ii) display, compared to the isolated natural CD4+ regulatory T-cells provided in (i), undetectable expression of the transcription repressor Foxp3, and increased activity of serine-threonine kinase AKT.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Artificial Sequence
<220> FEATURE:
<223> OTHER INFORMATION: synthetic peptide, amino acids 21-35 of Der p2
      allergen

<400> SEQUENCE: 1

Cys His Gly Ser Glu Pro Cys Ile Ile His Arg Gly Lys Pro Phe
1               5                   10                  15

<210> SEQ ID NO 2
<211> LENGTH: 22
<212> TYPE: PRT
<213> ORGANISM: Artificial Sequence
<220> FEATURE:
<223> OTHER INFORMATION: synthetic peptide, modified MOG T-cell epitope
<220> FEATURE:
<221> NAME/KEY: MISC_FEATURE
<222> LOCATION: (1)..(4)
<223> OTHER INFORMATION: thioreductase motif
<220> FEATURE:
<221> NAME/KEY: MISC_FEATURE
```

```
<222> LOCATION: (5)..(6)
<223> OTHER INFORMATION: Gly-Gly linker

<400> SEQUENCE: 2

Cys Gly Pro Cys Gly Gly Tyr Arg Ser Pro Phe Ser Arg Val Val His
1               5                   10                  15

Leu Tyr Arg Asn Gly Lys
            20

<210> SEQ ID NO 3
<211> LENGTH: 15
<212> TYPE: PRT
<213> ORGANISM: Artificial Sequence
<220> FEATURE:
<223> OTHER INFORMATION: synthetic peptide, modified HAdV-5 T-cell
      epitope
<220> FEATURE:
<221> NAME/KEY: MISC_FEATURE
<222> LOCATION: (1)..(4)
<223> OTHER INFORMATION: thioreductase motif
<220> FEATURE:
<221> NAME/KEY: MISC_FEATURE
<222> LOCATION: (5)..(6)
<223> OTHER INFORMATION: Gly-Gly linker

<400> SEQUENCE: 3

Cys Gly Pro Cys Gly Gly Tyr Val Pro Phe His Ile Gln Val Pro
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: synthetic peptide, modified chicken ovalbumin
      T-cell epitope
<220> FEATURE:
<221> NAME/KEY: MISC_FEATURE
<222> LOCATION: (1)..(4)
<223> OTHER INFORMATION: thioreductase motif
<220> FEATURE:
<221> NAME/KEY: MISC_FEATURE
<222> LOCATION: (5)..(6)
<223> OTHER INFORMATION: Gly-Gly linker

<400> SEQUENCE: 4

Cys Gly His Cys Gly Gly Ala Ala His Ala Glu Ile Asn Glu Ala Gly
1               5                   10                  15

Arg

<210> SEQ ID NO 5
<211> LENGTH: 17
<212> TYPE: PRT
<213> ORGANISM: Artificial Sequence
<220> FEATURE:
<223> OTHER INFORMATION: synthetic peptide, modified Der p2 T-cell
      epitope
<220> FEATURE:
<221> NAME/KEY: MISC_FEATURE
<222> LOCATION: (1)..(4)
<223> OTHER INFORMATION: thioreductase motif
<220> FEATURE:
<221> NAME/KEY: MISC_FEATURE
<222> LOCATION: (5)..(6)
<223> OTHER INFORMATION: Gly-Gly linker

<400> SEQUENCE: 5

Cys His Gly Cys Gly Gly Glu Pro Cys Ile Ile His Arg Gly Lys Pro
1               5                   10                  15
```

Phe

<210> SEQ ID NO 6
<211> LENGTH: 16
<212> TYPE: PRT
<213> ORGANISM: Artificial Sequence
<220> FEATURE:
<223> OTHER INFORMATION: synthetic peptide, MOG T-cell epitope, amino
      acids 40-55 of MOG

<400> SEQUENCE: 6

Tyr Arg Ser Pro Phe Ser Arg Val Val His Leu Tyr Arg Asn Gly Lys
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: synthetic peptide, amino acids 2144-2161 of
      human factor VIII

<400> SEQUENCE: 7

Ile Ile Ala Arg Tyr Ile Arg Leu His Pro Thr His Tyr Ser Ile Arg
1               5                   10                  15

Ser Thr

<210> SEQ ID NO 8
<211> LENGTH: 19
<212> TYPE: PRT
<213> ORGANISM: Artificial Sequence
<220> FEATURE:
<223> OTHER INFORMATION: synthetic peptide, modified Derp1 T-cell
      epitope
<220> FEATURE:
<221> NAME/KEY: MISC_FEATURE
<222> LOCATION: (1)..(4)
<223> OTHER INFORMATION: thioreductase motif

<400> SEQUENCE: 8

Cys Gly Phe Ser Ser Asn Tyr Cys Gln Ile Tyr Pro Pro Asn Ala Asn
1               5                   10                  15

Lys Ile Arg

<210> SEQ ID NO 9
<211> LENGTH: 15
<212> TYPE: PRT
<213> ORGANISM: Artificial Sequence
<220> FEATURE:
<223> OTHER INFORMATION: synthetic peptide, amino acids 71-85 of Der p2
      allergen

<400> SEQUENCE: 9

Asn Ala Cys His Tyr Met Lys Cys Pro Leu Val Lys Gly Gln Gln
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic peptide, mutated Der p2 allergen with
      Ser to Ala mutation at position 4

<400> SEQUENCE: 10

Cys His Gly Ala Glu Pro Cys Ile Ile His Arg Gly Lys Pro Phe
1               5                   10                  15

-continued

```
<210> SEQ ID NO 11
<211> LENGTH: 9
<212> TYPE: PRT
<213> ORGANISM: Artificial Sequence
<220> FEATURE:
<223> OTHER INFORMATION: synthetic peptide, amino acids 188-196 of
      glycoprotein D of human herpesvirus 1

<400> SEQUENCE: 11

Thr Tyr Leu Arg Leu Val Lys Ile Asn
1               5

<210> SEQ ID NO 12
<211> LENGTH: 13
<212> TYPE: PRT
<213> ORGANISM: Artificial Sequence
<220> FEATURE:
<223> OTHER INFORMATION: synthetic peptide, thioreductase motif coupled
      to amino acids 188-196 of glycoprotein D of human herpesvirus 1
<220> FEATURE:
<221> NAME/KEY: MISC_FEATURE
<222> LOCATION: (1)..(4)
<223> OTHER INFORMATION: thioreductase motif

<400> SEQUENCE: 12

Cys Gly His Cys Thr Tyr Leu Arg Leu Val Lys Ile Asn
1               5                   10

<210> SEQ ID NO 13
<211> LENGTH: 15
<212> TYPE: PRT
<213> ORGANISM: Artificial Sequence
<220> FEATURE:
<223> OTHER INFORMATION: synthetic peptide, amino acids 114-128 of Der
      p1 allergen

<400> SEQUENCE: 13

Ser Asn Tyr Cys Gln Ile Tyr Pro Pro Asn Ala Asn Lys Ile Arg
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: synthetic peptide, amino acids 324-340 of
      chicken ovalbumin

<400> SEQUENCE: 14

Ile Ser Gln Ala Val His Ala Ala His Ala Glu Ile Asn Glu Ala Gly
1               5                   10                  15

Arg

<210> SEQ ID NO 15
<211> LENGTH: 28
<212> TYPE: PRT
<213> ORGANISM: Mus musculus

<400> SEQUENCE: 15

Cys Ala Ala Arg Ser Ser Gly Ser Trp Gln Leu Ile Phe Gly Ser Gly
1               5                   10                  15

Thr Gln Leu Thr Val Met Pro Asp Ile Gln Asn Pro
            20                  25

<210> SEQ ID NO 16
```

```
<211> LENGTH: 25
<212> TYPE: PRT
<213> ORGANISM: Mus musculus

<400> SEQUENCE: 16

Cys Val Val Gly Asp Arg Gly Ser Ala Leu Gly Arg Leu His Phe Gly
1               5                   10                  15

Ala Gly Thr Gln Leu Ile Val Ile Pro
            20                  25

<210> SEQ ID NO 17
<211> LENGTH: 6
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (6)..(6)
<223> OTHER INFORMATION: Xaa denotes the N-terminal amino acid of a
      T-cell epitope

<400> SEQUENCE: 17

Cys Xaa Xaa Cys Gly Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (7)..(7)
<223> OTHER INFORMATION: Xaa denotes the N-terminal amino acid of a
      T-cell epitope

<400> SEQUENCE: 18

Cys Xaa Xaa Cys Gly Gly Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (8)..(8)
<223> OTHER INFORMATION: Xaa denotes the N-terminal amino acid of a
      T-cell epitope

<400> SEQUENCE: 19

Cys Xaa Xaa Cys Ser Ser Ser Xaa
```

```
<210> SEQ ID NO 20
<211> LENGTH: 9
<212> TYPE: PRT
<213> ORGANISM: Artificial Sequence
<220> FEATURE:
<223> OTHER INFORMATION: synthetic peptide, thioreductase motif with
      linker sequence
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (9)..(9)
<223> OTHER INFORMATION: Xaa denotes the N-terminal amino acid of a
      T-cell epitope

<400> SEQUENCE: 20

Cys Xaa Xaa Cys Ser Gly Ser Gly Xaa
1               5
```